United States Patent
Reichert et al.

(10) Patent No.: US 7,754,273 B2
(45) Date of Patent: Jul. 13, 2010

(54) METHOD OF PRINTING A TIME-TEMPERATURE INDICATOR BASED ON AZO COUPLING REACTIONS ONTO A SUSBTRATE

(75) Inventors: Hans Reichert, Rheinfelden (DE); Bernhard Müller, Efringen-Kirchen (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 696 days.

(21) Appl. No.: 11/659,578

(22) PCT Filed: Aug. 3, 2005

(86) PCT No.: PCT/EP2005/053786
§ 371 (c)(1), (2), (4) Date: Feb. 7, 2007

(87) PCT Pub. No.: WO2006/015962
PCT Pub. Date: Feb. 16, 2006

(65) Prior Publication Data
US 2007/0218206 A1    Sep. 20, 2007

(30) Foreign Application Priority Data
Aug. 11, 2004    (EP) .................................. 04103872

(51) Int. Cl.
| G01N 31/00 | (2006.01) |
| G01N 33/00 | (2006.01) |
| B41M 5/00 | (2006.01) |
| C09D 11/00 | (2006.01) |
| C09K 9/00 | (2006.01) |
| G01K 3/00 | (2006.01) |

(52) U.S. Cl. ................................ 427/7; 436/2; 534/581
(58) Field of Classification Search ................ 534/581; 427/7; 436/2
See application file for complete search history.

(56) References Cited

U.S. PATENT DOCUMENTS

| 3,999,946 A | 12/1976 | Patel et al. ..................... 23/253 |
| 5,053,339 A | 10/1991 | Patel .............................. 436/2 |
| 5,476,792 A | 12/1995 | Ezrielev et al. ................. 436/1 |
| 6,214,623 B1 | 4/2001 | Simons et al. .................. 436/2 |
| 6,514,462 B1 | 2/2003 | Simons ................... 422/82.12 |
| 6,544,925 B1 * | 4/2003 | Prusik et al. ................. 503/201 |
| 2004/0083560 A1 * | 5/2004 | Adam et al. .................... 8/432 |

FOREIGN PATENT DOCUMENTS

| EP | 0 930 488 | 7/1999 |
| EP | 0 930 489 | 7/1999 |
| JP | 11-109064 | 4/1999 |
| WO | 91/09287 | 6/1991 |

OTHER PUBLICATIONS

English Language Abstract from Patent Abstracts of Japan for JP 11-109064 (1999).

* cited by examiner

*Primary Examiner*—Michael Barr
*Assistant Examiner*—Ryan Schiro
(74) *Attorney, Agent, or Firm*—Tyler A. Stevenson

(57) ABSTRACT

The present invention relates to a method of printing a substrate, comprising (a) printing onto the substrate at least one time temperature indicator with chromic properties based on an azo coupling reaction between a capped diazonium component and a coupling component.

19 Claims, No Drawings

METHOD OF PRINTING A TIME-TEMPERATURE INDICATOR BASED ON AZO COUPLING REACTIONS ONTO A SUSBTRATE

The present invention relates to a method of printing a substrate, comprising (a) printing onto the substrate a time-temperature indicator (TTI) which comprises at least one indicator having chromic properties based on azo coupling reactions between a stabilized diazonium ion and a coupling compound.

When perishable materials are used it is often desirable to ascertain the age and the current usable condition of the materials. While the application of an expiry date to the packaging was formerly considered sufficient, for a large number of products such a procedure is nowadays too inaccurate and insufficiently tamper-proof. In particular, the condition of perishable products is generally a function not only of time but also of other variables, such as, especially, temperature.

U.S. Pat. No. 3,999,946 addresses this problem and proposes providing the perishable products with an indicator giving the time/temperature history. According to the length of storage and the storage temperature of the product, the originally colourless acetylene-based indicator exhibits a characteristic, irreversible colour change from which the quality of the stored perishable product can be inferred.

EP-A-1 17 390 also describes a time-temperature indicator based on diacetylene materials, wherein the change in the reflectance of the diacetylene materials is measured and the diacetylene materials are applied to the substrate by means of customary printing techniques, such as flexographic printing, intaglio printing, screen printing, ink-jet printing or letterpress printing.

Further U.S. Pat. No. 5,053,339 describes a time-temperature indicator (TTI) which consists of a layer comprising the indicator, a barrier layer that is impermeable to the indicator and permeable to the activator, and a layer comprising the activator. In dependence upon the temperature, the activator diffuses through the barrier layer into the indicator layer, where it provides a change in colour.

In principle, almost every color-forming reaction is suitable within a time temperature indicator format if the reaction is adjustable to the decomposition rate of the perishable good at various temperatures. For example, WO 99/39197 describes a time-temperature indicator comprising at least one reversible indicator having photochromic properties based on transfer reactions. The nature and the amount of the TTI used for printing can be matched to the perishable products. The TTI can be used both in the form of a solution and an aqueous dispersion.

Azoic dyes and their use for dyeing in which an insoluble azo dye is produced directly onto or within a fibre has been known for a long time. Diazonium ions are produced when for example an aryl amine is reacted in aqueous solution with a dissolved nitrite of an alkali metal in the presence of hydrochloric acid or alternatively, with an organic nitrite, e.g. t-butylnitrite in an organic solvent. A diazonium ion is a reactive intermediate that is capable to undergo substitution or coupling reactions. For example, groups like halogen, cyamide, hydroxyl or hydrogen may substitute for a diazo group bonded to an arene ($ArN_2^+$). Compounds such as aniline and phenol, which contain strong electron donating groups (e.g., —OH and —$NH_2$) that activate the ortho and para positions on a benzene ring, can undergo coupling reactions with a diazonium ion. The mechanism of a coupling reaction is an electrophilic aromatic substitution reaction.

In the prior art, the use of azo coupling reactions within a time temperature indicator format has neither been described nor suggested. This is mainly because of the fact that one of the starting materials, the diazotized amine is too unstable to be handled within a TTI.

Thus, there is a need for a time temperature indicator that is based on an azo coupling reaction wherein the color-forming azo coupling can be controlled and sufficiently adjusted to the decomposition rate of a perishable good at various temperatures and therefore can form the basis of a novel time temperature indicator format.

The problem according to the invention is solved by a method of determining the quality of an ageing- and temperature-sensitive product, which comprises the following steps:
(a) printing onto a substrate at least one time temperature indicator with chromic properties based on an azo coupling reaction between a capped diazonium component and a coupling component,
(b) activating, preferably by photo-induced acidification, of the time temperature indicator,
(c) optionally applying of a protector which prevents continued photo-induced acidification of the indicator, and
(d) determining the degree of time- or temperature-induced coloration and deducing the quality of the product from the degree of coloration; or by a method of printing a substrate, comprising
(a) printing onto the substrate at least one time temperature indicator with chromic properties based on an azo coupling reaction between a capped diazonium component and a coupling component.

Preferably, the printing step (a) is carried out using the ink-jet printing technology wherein the at least one time temperature indicator with chromic properties based on an azo coupling reaction between a capped diazonium component and a coupling component is transferred to a suitable substrate by directly jetting ink droplets from very fine nozzles to the substrate and depositing the ink droplets on it.

An azo coupling reaction is generally to be understood as being a reaction wherein a diazonium salt is reacted with a coupling compound (for example a aromatic or heteroaromatic compound) to form a stable azo dye or pigment. Generally, diazo compounds are derived from primary arylamines following treatment with either an alkali metal nitrite and hydrochloric acid in aqueous solution or an organic nitrite in a non-aqueous solution. Diazo compounds can be described as containing the $N_2$ grouping combined to only one hydrocarbon radical instead of two as in azo compounds. The formation of diazo compounds depends upon the replacement of three hydrogen atoms of the salt of an aryl primary amine by nitrogen from the inorganic or organic nitrite to form the so-called diazonium salts. For example, azo dyes are obtained by coupling a phenol or naphthol to a diazonium compound. Compounds with phenolic hydroxyl groups, naphthols and analogues, primary (and some secondary) arylamines, aromatic compounds with a reactive methylene group capable of enolization, including derivatives of acetoacetic ester and arylamines, some heterocycles such as pyrrole, indole and imidazole, o-alkylphenols, naphthols and N-acylamines, including phenol and naphthol ethyl ethers and acetylnaphthylamines, aliphatic enols such as ethyl acetoacetate, and compounds containing an alicyclic carbon such as ascorbic acid or dimedone are compounds capable of being coupling components with diazonium compounds.

By virtue of its chromic properties, the indicator can undergo a time- and temperature-dependent coloration due to the formation of an azo dye or pigment. The coloration process of the indicator can start at a defined timepoint, preferably, for example, immediately after printing of the substrate, which is especially the packaging of a perishable material. The time-temperature clock can accordingly be started at a defined desired timepoint and does not necessarily begin to run at the time of the indicator synthesis. Coloration is preferred for consideration according to the invention, but the use of an indicator in which a color change process when at least one of the starting compounds is also colored forms the basis of the time-temperature clock is also conceivable.

It is also possible to use two or more indicators having different time domains; that is to say it is possible to use, for example, two or more indicators based on different azo coupling reactions, optionally in combination with other indicators, for example those indicating storage of the perishable product at too high temperature.

The actual determination of the quality of ageing- or temperature-sensitive products is preceded by the activation of the time temperature indicator. The coloration process is initiated by lowering the pH to a value of from 6.5 to 1.5, preferably from 4 to 3. This can be achieved for example by adding an acid or an acidic buffer solution or by the irradiation of a photolatent acid that is present in the reaction medium to form an active acid catalyst.

The rate of the azo coupling reaction strongly depends on the pH value of the reaction medium. At various time points of the reaction, different color shades depending on the concentration of the azo product already formed can be observed. The instant invention therefore provides a variety of different time temperature indicators based on a single azo coupling chemistry in that the coupling reaction is carried out at different pH values. It will be understood that a specific pH can easily be adjusted by picking a suitable buffer system well known to one skilled in the art.

At a later timepoint, the degree of time- or temperature-induced coloration is then measured and the quality of the product is inferred therefrom. When an evaluation is made with the aid of the human eye, it may be advantageous to arrange e.g. alongside or below the substrate a reference scale which allocates a certain quality grade, a certain timepoint etc. to a certain degree of decoloration.

The method according to the invention is suitable for marking perishable products such as foodstuffs (e.g. frozen foods), medicaments, drugs, transplant organs and perishable raw materials.

It is generally the case that, depending upon the chemical nature of the azo coupling reaction and especially according to the reactivity of both the diazonium salt and the coupling compound and the pH value of the reaction medium, it is possible to achieve different lengths of decoloration time.

Preferably, the method of printing a substrate according to the invention comprises (a) printing onto the substrate at least one time temperature indicator with chromic properties based on an azo coupling reaction between a capped diazonium component and a coupling component wherein the capped diazonium component and the coupling component are printed as a single solution onto the substrate. Alternatively, it is also possible that the capped diazonium component and the coupling component are printed as separate solutions onto the substrate.

It is preferred when the substrate is a packaging material or a label applied to the packaging material.

Examples of preferred capped diazonium components are compounds of formulae (1), (2), (3), (4) and (5)

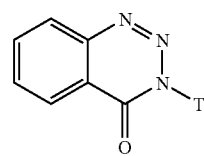

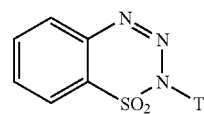

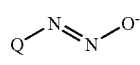

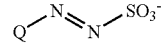

wherein

Q is a radical of an organic compound,

R is the radical of an unsubstituted or substituted aliphatic or aromatic amine, and T is an unsubstituted or substituted, aliphatic or aromatic residue.

Examples of more preferred capped diazonium components are compounds of formulae (1), (2), (3), (4) and (5)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl; or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by $C_1$-$C_4$alkyl, $C_1$-$C_4$alkoxy, $C_1$-$C_4$alkylthio, halogen, e.g. fluorine, bromine or chlorine, nitro, trifluoromethyl, CN, SCN, $C_1$-$C_4$alkylsulfonyl, phenylsulfonyl, benzylsulfonyl, di-$C_1$-$C_4$alkylaminosulfonyl, $C_1$-$C_4$alkyl-carbonylamino, $C_1$-$C_4$alkoxysulfonyl or by di-(hydroxy-$C_1$-$C_4$alkyl)-aminosulfonyl;

or Q is a cationic radical of an organic compound; and

R is a radical of formula —$NR_{16}R_{17}$, wherein $R_{16}$ is hydrogen; unsubstituted linear or branched $C_1$-$C_6$alkyl or linear or branched $C_1$-$C_6$alkyl, which is substituted by one or more identical or different substituent selected from the group consisting of $OC_1$-$C_4$alkyl, COOH, $COOC_1$-$C_2$alkyl, $SO_3H$, $NH_2$, CN, halogen and OH, and $R_{17}$ is unsubstituted linear or branched $C_1$-$C_6$alkyl or linear or branched $C_1$-$C_6$alkyl, which is substituted by one or more identical or different substituent selected from the group consisting of $OC_1$-$C_4$alkyl, COOH, $COOC_1$-$C_2$alkyl, $SO_3H$, $NH_2$, CN, halogen and OH; or R is the radical of unsubstituted aniline; the radical of unsubstituted aminonaphthalene; the radical of aniline or aminonaphthalene, wherein the phenyl or the naphthyl ring is substituted by one or more identical or different substituent selected from the group consisting of COOH, SO$_3$H, CN, halogen, SO$_2$C$_1$-C$_2$alkyl, unsubstituted linear or branched C$_1$-C$_4$alkyl, linear or branched C$_1$-C$_4$alkyl, substituted by OH, carboxy, COC$_1$-C$_2$alkyl or SO$_2$—N(C$_1$-C$_4$alkyl)-(CH$_2$)$_{1-4}$SO$_3$H and wherein the amino radical is substituted by hydrogen, unsubstituted linear or branched C$_1$-C$_4$alkyl or linear or branched C$_1$-C$_4$alkyl, substituted by OH or carboxy; and T is a linear or branched unsubstituted C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, NH(C$_1$-C$_2$alkyl), N(C$_1$-C$_2$alkyl)$_2$, CN, halogen and OH; or T is unsubstituted phenyl; unsubstituted naphthyl; phenyl or naphthyl, which are substituted by one or more identical or different substituents selected from the group consisting of OC$_1$-C$_4$alkyl, COOH, COOC$_1$-C$_2$alkyl, SO$_3$H, NH$_2$, NH(C$_1$-C$_2$alkyl), N(C$_1$-C$_2$alkyl)$_2$, CN, halogen and OH.

Even more preferred examples of the capped diazonium components are compounds of formulae (1), (2), (3), (4) and (5)

wherein

Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl; or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by C$_1$-C$_4$alkyl, C$_1$-C$_4$alkoxy, C$_1$-C$_4$alkylthio, halogen, e.g. fluorine, bromine or chlorine, nitro, trifluoromethyl, CN, SCN, C$_1$-C$_4$alkylsulfonyl, phenylsulfonyl, benzylsulfonyl, di-C$_1$-C$_4$alkylaminosulfonyl, C$_1$-C$_4$alkyl-carbonylamino, C$_1$-C$_4$alkoxysulfonyl or by di-(hydroxy-C$_1$-C$_4$alkyl)-aminosulfonyl;

or Q is cationic radical of an organic compound; and

R is a radical of formula —NR$_{16}$R$_{17}$, wherein R$_{16}$ is hydrogen; unsubstituted linear or branched C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, CN, halogen and OH, and R$_{17}$ is unsubstituted linear or branched C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, CN, halogen and OH; and T is a linear or branched C$_1$-C$_6$alkyl, which is substituted by one or two identical or different substituent selected from the group consisting of COOH, SO$_3$H, NH$_2$, NH(C$_1$-C$_2$alkyl) and N(C$_1$-C$_2$alkyl)$_2$, or T is unsubstituted phenyl; unsubstituted naphthyl; phenyl or naphthyl, which are substituted by one or more identical or different substituents selected from the group consisting of OC$_1$-C$_4$alkyl, COOH, COOC$_1$-C$_2$alkyl, SO$_3$H, NH$_2$, NH(C$_1$-C$_2$alkyl), N(C$_1$-C$_2$alkyl)$_2$, CN, halogen and OH.

Particularly preferred examples of capped diazonium components of formula (I) include compounds wherein Q is an unsubstituted phenyl; naphthyl; thiophenyl; 1,3-thiazolyl; 1,2-thiazolyl; 1,3-benzothiazolyl; 2,3-benzothiazolyl; imidazolyl; 1,3,4-thiadiazolyl; 1,3,5-thiadiazolyl; 1,3,4-triazolyl; pyrazolyl; benzimidazolyl; benzopyrazolyl; pyridinyl; quinolinyl; pyrimidinyl; isoxazolyl; aminodiphenyl; aminodiphenylether and azobenzenyl; or Q is a phenyl, naphthyl, thiophenyl, 1,3-thiazolyl, 1,2-thiazolyl, 1,3-benzothiazolyl, 2,3-benzothiazolyl, imidazolyl, 1,3,4-thiadiazolyl, 1,3,5-thiadiazolyl, 1,3,4-triazolyl, pyrazolyl, benzimidazolyl, benzopyrazolyl, pyridinyl, quinolinyl, pyrimidinyl and isoxazolyl, aminodiphenyl, aminodiphenylether and azobenzenyl which is mono- or poly-substituted by C$_1$-C$_4$alkyl, C$_1$-C$_4$alkoxy, C$_1$-C$_4$alkylthio, halogen, e.g. fluorine, bromine or chlorine, nitro, trifluoromethyl, CN, SCN, C$_1$-C$_4$alkylsulfonyl, phenylsulfonyl, benzylsulfonyl, di-C$_1$-C$_4$alkylaminosulfonyl, C$_1$-C$_4$alkyl-carbonylamino, C$_1$-C$_4$alkoxysulfonyl or by di-(hydroxy-C$_1$-C$_4$alkyl)-aminosulfonyl;

or Q is a cationic radical of an organic compound;

R is a radical of formula —NR$_{16}$R$_{17}$, wherein R$_{16}$ is H; unsubstituted linear or branched C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, CN, halogen and OH, and R$_{17}$ is unsubstituted linear or branched C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, CN, halogen and OH.

More preferred examples of capped diazonium components of formula (I) are compounds wherein Q is a cationic radical of an organic compound;

R is a radical of formula —NR$_{16}$R$_{17}$, wherein R$_{16}$ is H; unsubstituted linear or branched C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, CN, halogen and OH, and R$_{17}$ is unsubstituted linear or branched C$_1$-C$_6$alkyl or linear or branched C$_1$-C$_6$alkyl, which is substituted by one or more identical or different substituent selected from the group consisting of OC$_1$-C$_4$alkyl, COOH, COOC$_1$-C$_2$alkyl, SO$_3$H, NH$_2$, CN, halogen and OH.

Most preferred examples of capped diazonium components of formula (I) are compounds wherein Q is a radical of formula

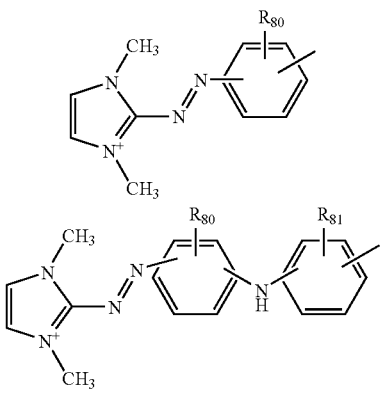

wherein $R_{80}$ and $R_{81}$, are independently from each other are hydrogen; unsubstituted or substituted linear or branched $C_1$-$C_6$alkyl, $OC_1$-$C_4$alkyl, COOH, $COOC_1$-$C_2$alkyl, $SO_3H$, $NH_2$, CN, halogen and OH; and R is a radical of formula —$NR_{16}R_{17}$, wherein $R_{16}$ is unsubstituted linear or branched $C_1$-$C_6$alkyl and $R_{17}$ is unsubstituted linear or branched $C_1$-$C_6$alkyl or linear or branched $C_1$-$C_6$alkyl, which is substituted by one or more identical or different substituent selected from the group consisting of $OC_1$-$C_4$alkyl, COOH, $COOC_1$-$C_2$alkyl, $SO_3H$, $NH_2$, CN, halogen and OH.

Especially preferred examples of the capped diazonium component include the compounds of the following general formula:

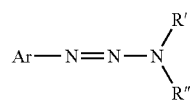

wherein Ar stands for an optionally substituted aryl or heteroaryl residue, in particular optionally substituted phenyl, naphthyl, pyrrolyl, furyl, thiophenyl, oxazolyl, isoxazolyl, thiazolyl, pyrazolyl and pyridinyl; and wherein R' and R" stand independently from each other for a linear or branched $C_1$-$C_6$alkyl, which is optionally substituted by one or two identical or different substituent selected from the group consisting of COOH, OH, halogen, $SO_3H$, $NH_2$, $NH(C_1$-$C_2$alkyl) and $N(C_1$-$C_2$alkyl)$_2$, in particular wherein R' and R" stand independently from each other for methyl,

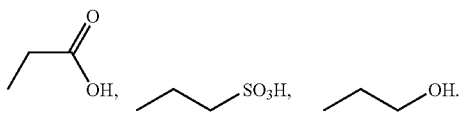

It is most preferred when the capped diazonium component is a compound of the following formulae:

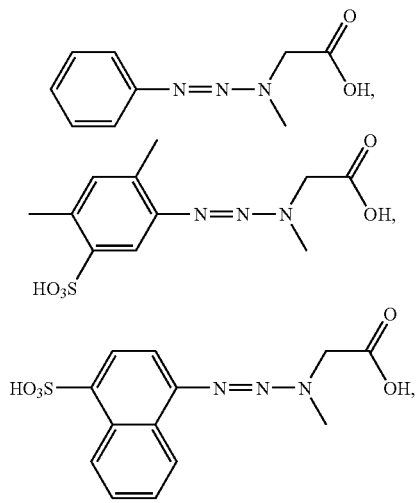

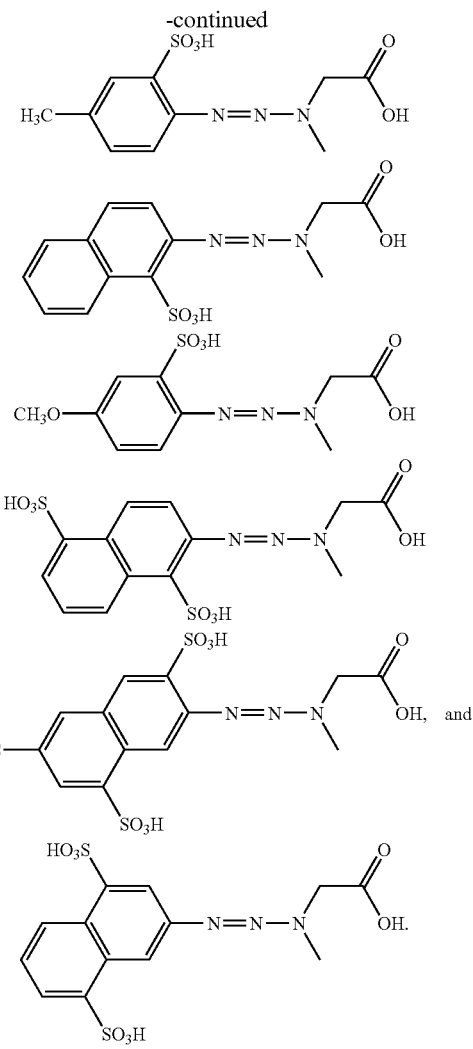

It will be understood that each —$SO_3H$ sulfonic acid group also represents any corresponding salt, e.g. an alkali metal, an alkaline-earth metal or an ammonium salt thereof.

Suitable coupling components are unsubstituted or substituted benzene or naphthalene compounds, open-chain methylene-active compounds and unsubstituted or substituted heterocyclic compounds.

It is preferred when the coupling compound is selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes and hydroxypyridines.

More preferably, the coupling component is selected from the group consisting of acetoacetanilides, phenols, anilines, diphenylamines, naphthylamines, indoles, quinolines, pyridones, pyrazoles and aminopyridines.

Optionally, the coupling component can carry one or more substituents selected from the group consisting of amino, alkylamino, dialkylamino, halogen, alkyl, alkoxy, aryl, preferably phenyl or naphthyl, aryloxy, hydroxy, carboxy, sulfo and quaternised ammonium radicals.

Preferred examples of the coupling component include the compounds of the following formulae:

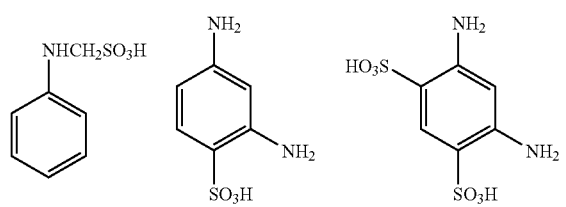
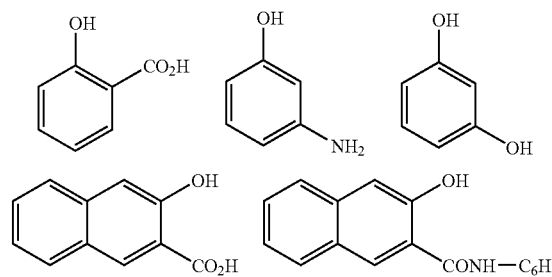
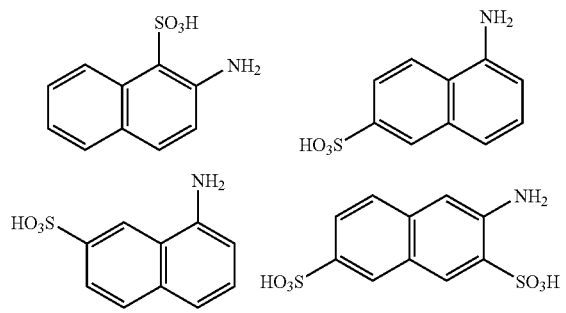
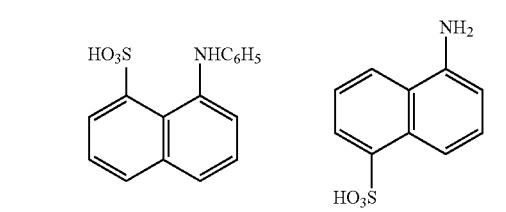
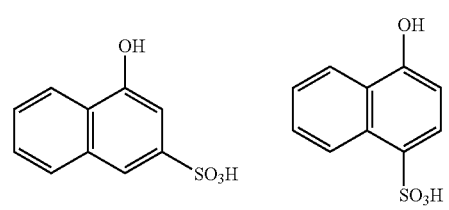
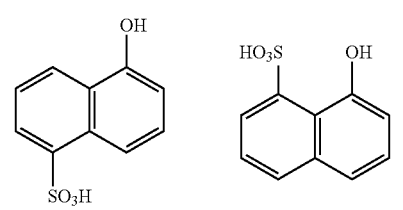
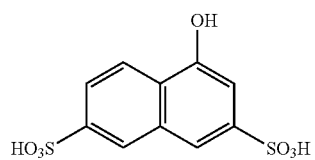
-continued
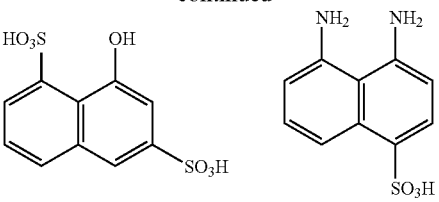
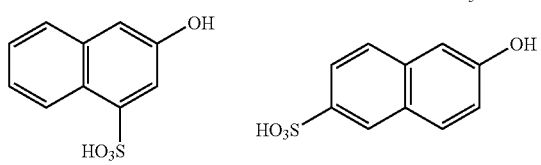
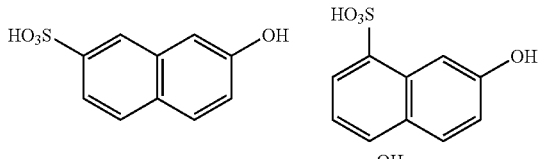
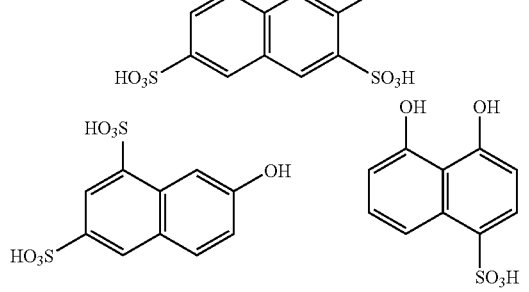
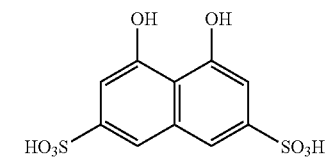
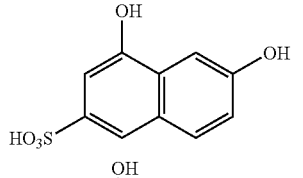
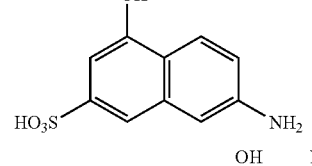
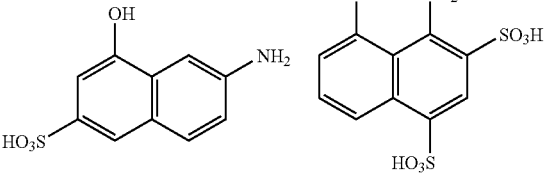
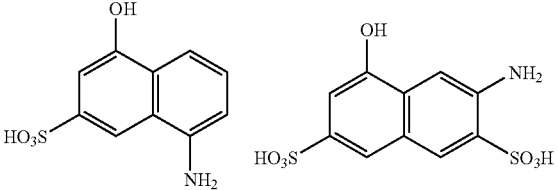

-continued
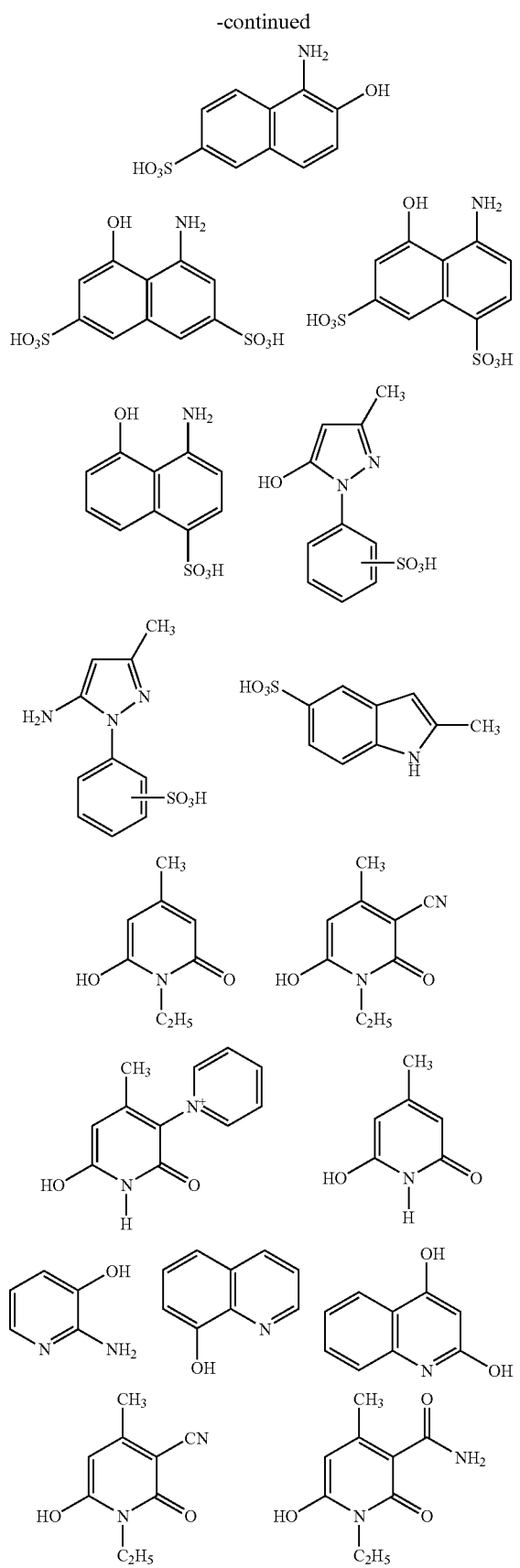
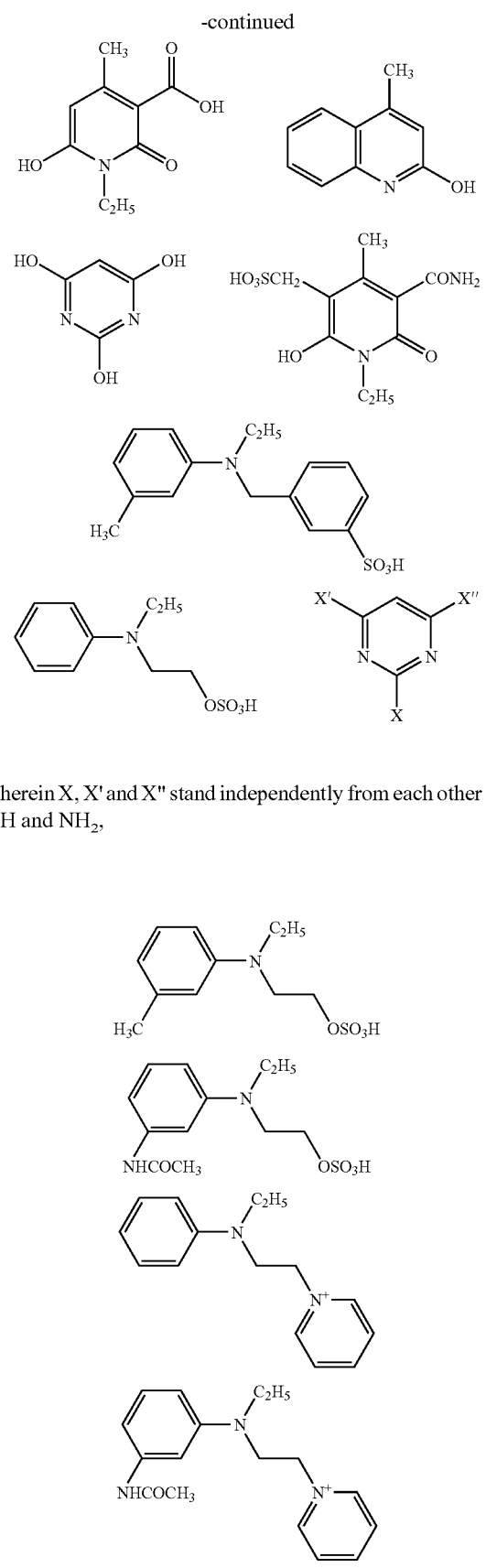
wherein X, X' and X" stand independently from each other for OH and $NH_2$, -continued

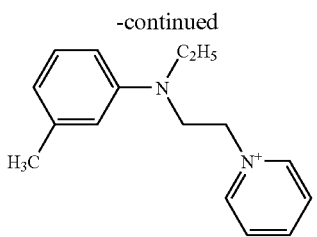

Especially preferred coupling component are selected from the group consisting of:

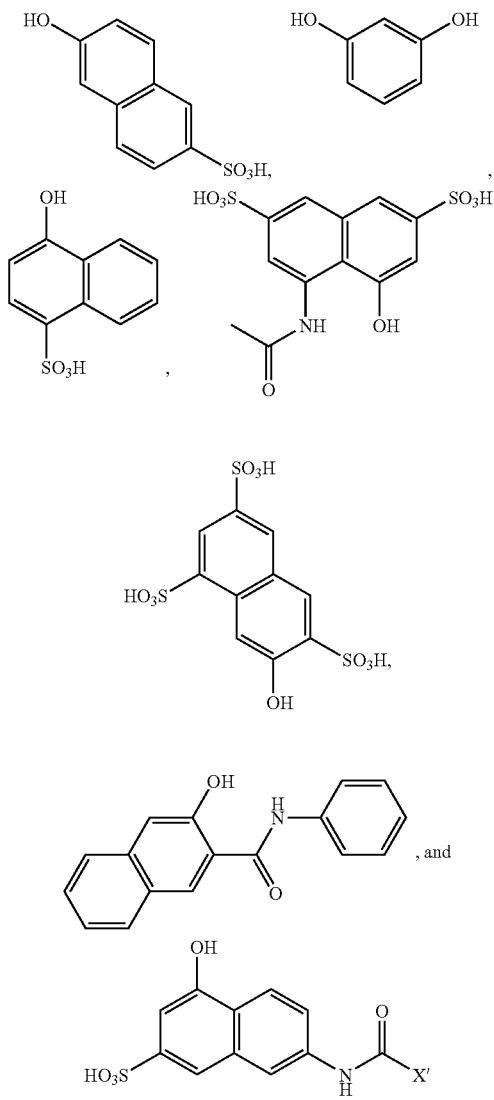

wherein X' stands for $C_1$-$C_6$-alkyl or —O—$C_1$-$C_6$-alkyl.

In another embodiment of the present invention, the capped diazonium component and the coupling component are moieties of a single compound.

Preferred compounds having both a moiety representing a capped diazonium component and a coupling component moiety are compounds of formula (6)

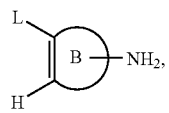

(6)

wherein L is hydroxy or $NHL_1$, $L_1$ being hydrogen or $C_1$-$C_4$alkyl, and B is an aromatic or heterocyclic ring.

More preferably, the single compound representing both a capped diazonium component and a coupling component moiety are selected from the group consisting of

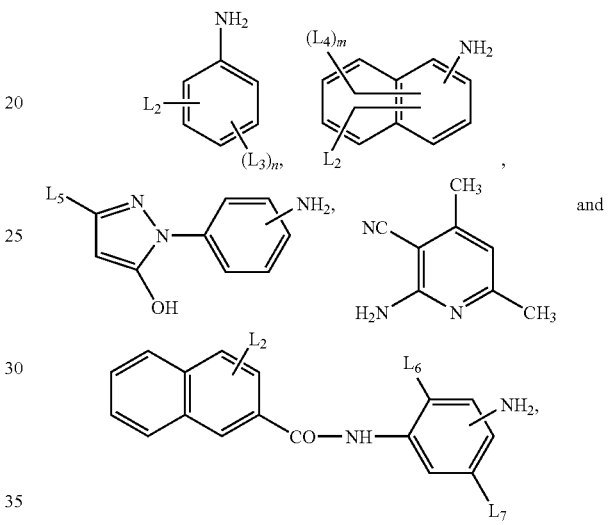

wherein $L_2$ is hydroxy or $NHL_1$, $L_1$ being hydrogen or $C_1$-$C_4$alkyl, $L_3$ is $C_1$-$C_4$alkyl or sulfo, $L_4$ is hydroxy or sulfo, $L_5$ is hydrogen, $C_1$-$C_4$alkyl, —COOH or COO$C_1$-$C_4$alkyl, $L_6$ and $L_7$ are, each independently of the other, hydrogen or $C_1$-$C_4$alkoxy, n is a number 0, 1 or 2, and m is a number 0, 1 or 2.

Especially preferred compounds having a capped diazonium component moiety and a coupling component moiety include the compounds of the following formulae:

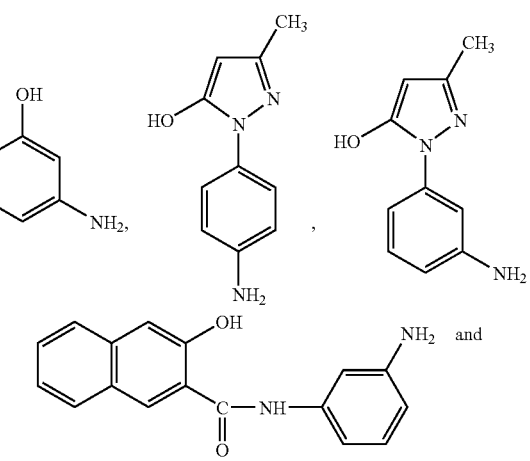

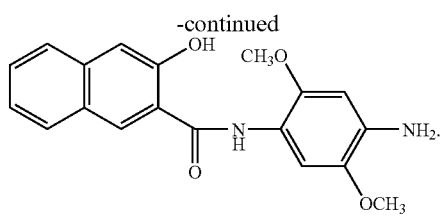
The azo coupling reaction between the capped diazonium component and the coupling component underlying the time temperature indicator according to the present invention preferably form an azo dye being selected from the group consisting of:
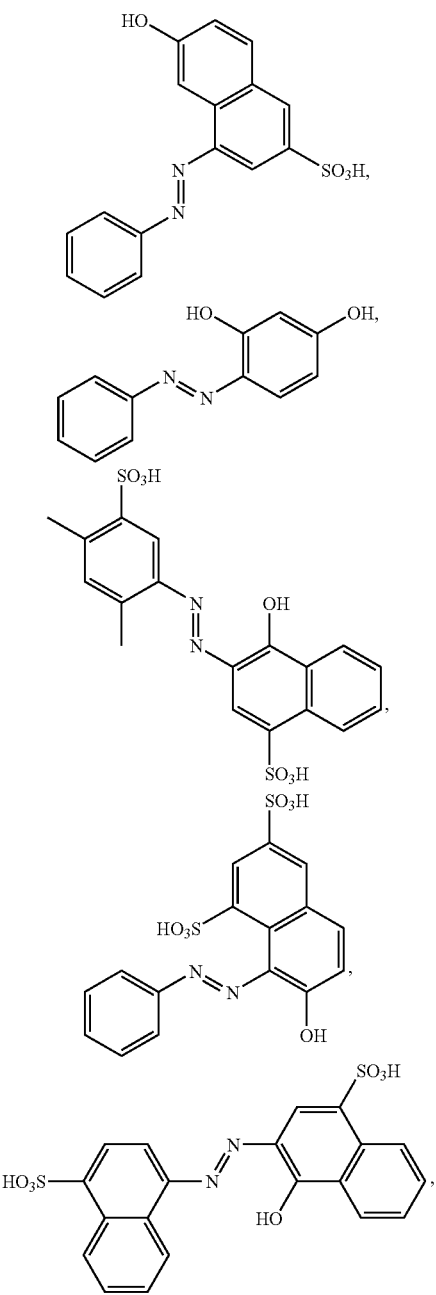
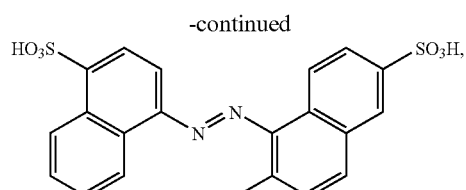
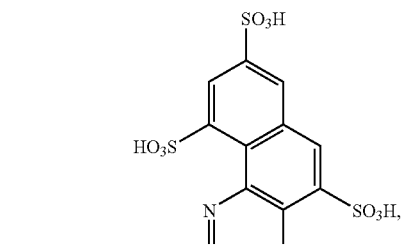
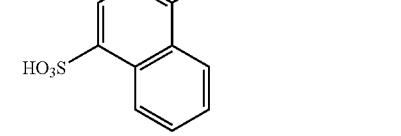
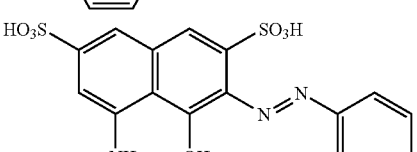
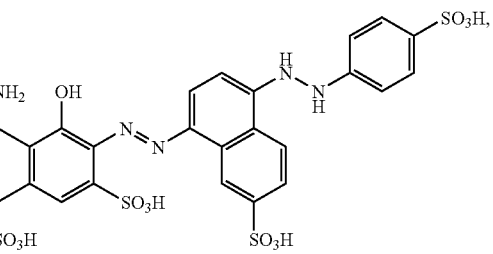
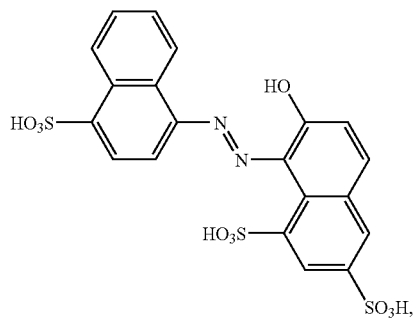

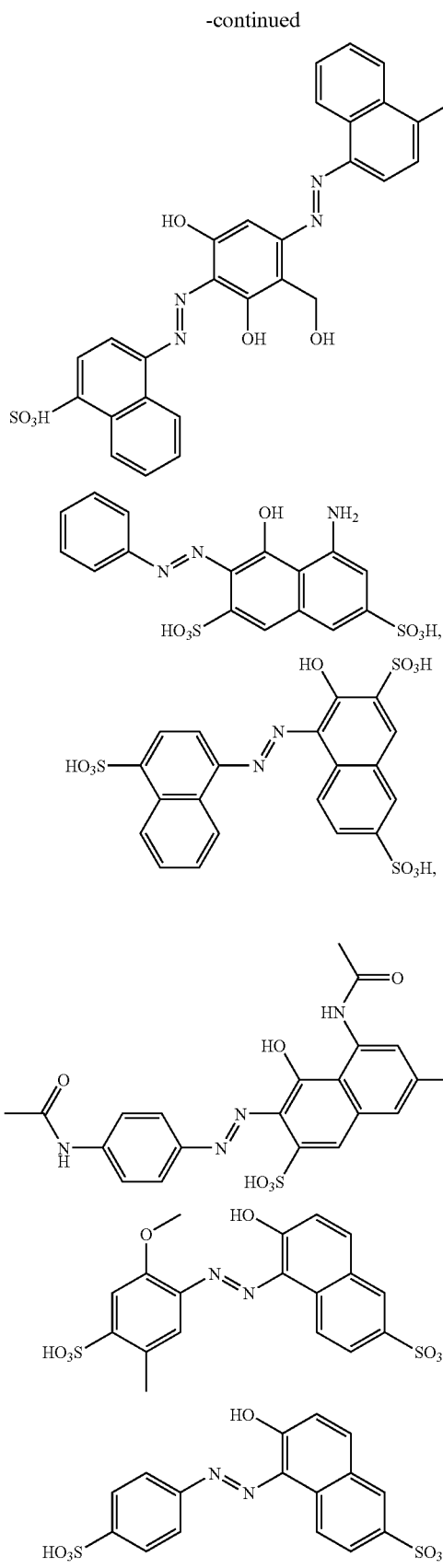

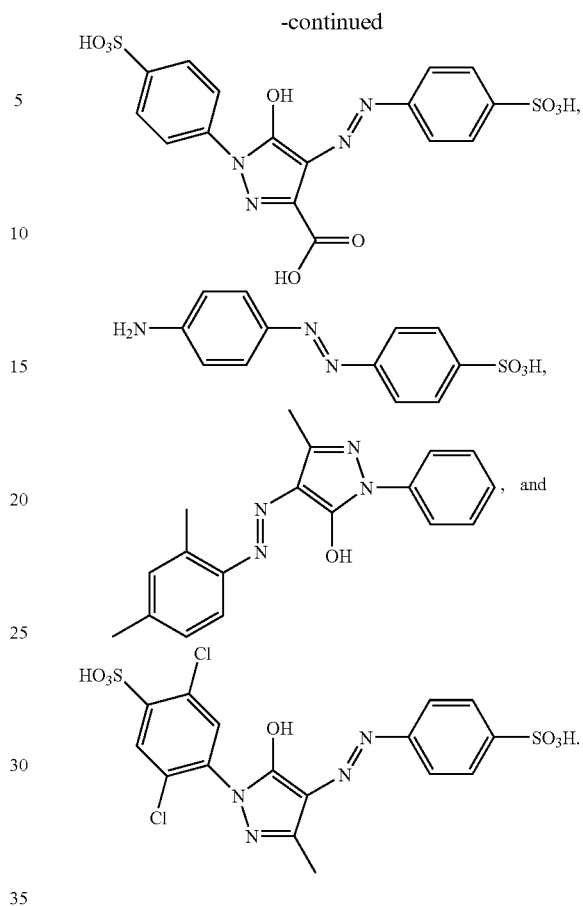

In yet another embodiment of the present invention, the capped diazonium component and/or the coupling component are capable to perform multiple azo coupling reactions leading to azo dyes containing more than one azo moieties. The second and any further azo coupling reaction takes either place by coupling of capped diazonium component to an already existing azo compound or alternatively, by diazotizing an azo compound followed by the coupling to an ordinary coupling component. The coupling products containing multiple azo groups can be distinguished by their different absorption maxima. Each additional azo coupling is generally accompanied by a remarkable color change so that the progress of the reaction can be visually followed. Preferably, the dyes formed during the TTI reaction according to the instant invention contain two azo groups.

In the method of printing a substrate according to the present invention, the time temperature indicator is activated following step (a) by acidifying the reaction medium which is preferably an aqueous solution. More preferably, the activation is achieved by lowering the pH to a value of from 6.5 to 1.5, most preferably from 4 to 3. The acidification can be accomplished in that the method of printing a substrate includes a step (b) comprising printing onto the substrate (i) an acid and/or an acidic buffer solution, or (ii) a photolatent acid solution.

Preferably, the acid and/or the acidic buffer solution (i), or the photolatent acid solution (ii) is printed onto the substrate in step (a) together with the capped diazonium component and/or the coupling component as part of a single solution. Suitable acids for acidification are selected from the group consisting of hydrochloric acid, phosphoric acid, sulfuric acid, acetic acid, trifluoroacetic acid, trifluoromethanesulfonic acid, gluconic acid, tartaric acid, malic acid fumaric, succinic acid and citric acid.

Examples of photolatent acids include oxime sulfonate compounds, α-sulfonyloxy carbonyl compounds, N-sulfonyloxyimide compounds, o-nitrobenzylsulfonate compounds and pyrogallol sulfonate compounds.

Preferred photolatent acids are compounds of formulae Ia, Ib, IIa, IIb, IIIa, IIIb, IVa, IVb, Va, Vb or VIa:

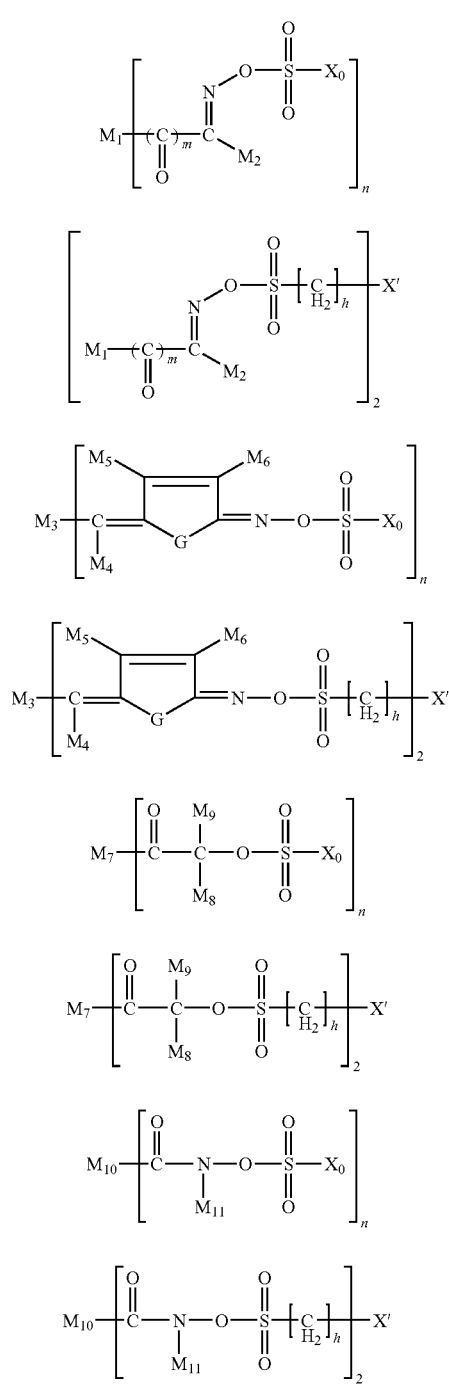

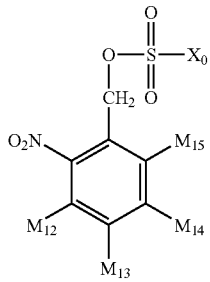

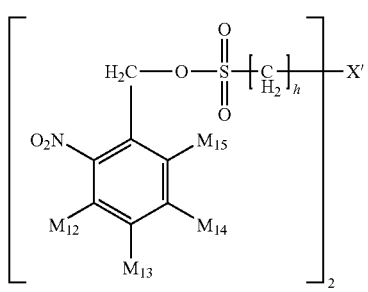

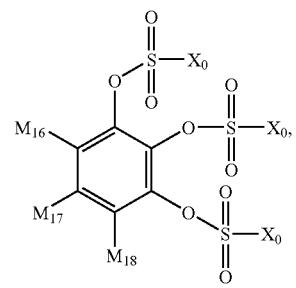

n is 1 or 2;
m is 0 or 1;
$X_0$ is $-[CH_2]_h-X$ or $-CH=CH_2$;
h is 2, 3, 4, 5 or 6;
$M_1$ when n is 1, is phenyl, naphthyl, anthracyl, phenanthryl, or heteroaryl,
all of which are optionally substituted by one or more $C_1$-$C_{18}$alkyl, $C_1$-$C_8$haloalkyl, $C_3$-$C_{30}$cycloalkyl; $C_3$-$C_{30}$cycloalkyl which is interrupted by one or more $-O-$, $-S-$, $-NM_{23}-$, $-O(CO)-$, or $-NM_{23}(CO)-$; or are substituted by halogen, $-NO_2$, $-CN$, $-Ar_1$, $-(CO)M_{19}$, $-(CO)OM_{20}$, $-(CO)NM_{21}M_{22}$, $-O(CO)M_{19}$, $-O(CO)OM_{20}$, $-O(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$, optionally the substituents $-(CO)M_{19}$, $-(CO)OM_{20}$, $-(CO)NM_{21}M_{22}$, $-O(CO)M_{19}$, $-O(CO)OM_{20}$, $-O(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$ form 5-, 6- or 7-membered rings, via the radicals $M_{19}$, $M_{20}$, $M_{21}M_{22}$ and/or $M_{23}$, with further substituents on the phenyl, naphthyl, anthracyl, phenanthryl, or heteroaryl ring or with one of the carbon atoms of the phenyl, naphthyl, anthracyl, phenanthryl, or heteroaryl ring;
or $M_1$ is hydrogen, with the proviso that $M_2$ is not simultaneously hydrogen; or $M_1$ is $C_1$-$C_{18}$alkyl; or is $C_2$-$C_{18}$alkyl which is interrupted by one or more C$_3$-C$_{30}$cycloalkylene, —O—, —S—, —NM$_{23}$-, —(CO)—, —O(CO)—, —S(CO)—, —NM$_{23}$(CO)—, —SO—, —SO$_2$—, or —OSO$_2$—; optionally the radicals C$_1$-C$_{18}$alkyl and C$_2$-C$_{18}$alkyl are substituted by one or more C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_1$ is C$_3$-C$_{30}$cycloalkyl, optionally interrupted by one or more —O—, —S—, —NM$_{23}$-, —(CO)—, —O(CO)—, or —NM$_{23}$(CO)—, and which is unsubstituted or substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_1$ is C$_1$-C$_8$haloalkyl, C$_2$-C$_{12}$alkenyl, C$_4$-C$_{30}$cycloalkenyl, camphoryl;

or if m is 0, M$_1$ additionally is CN, C$_2$-C$_6$alkoxycarbonyl or phenoxycarbonyl, wherein C$_2$-C$_6$alkoxycarbonyl and phenoxycarbonyl optionally are substituted by one or more C$_1$-C$_{18}$alkyl, C$_1$-C$_8$haloalkyl, C$_3$-C$_{30}$cycloalkyl; C$_3$-C$_{30}$cycloalkyl which is interrupted by one or more —O—, —S—, —NM$_{23}$-, —O(CO)—, or —NM$_{23}$(CO)—; or are substituted by halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

M$_1$, when n is 2, is phenylene, naphthylene,

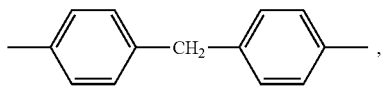

diphenylene, oxydiphenylene or

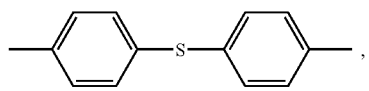

wherein these radicals are unsubstituted or substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$, or M$_1$ is a direct bond

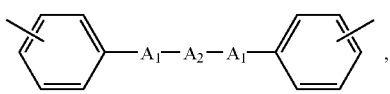

-continued

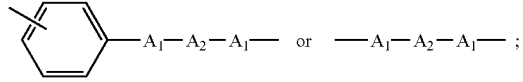

wherein all radicals M$_1$ with the exception of hydrogen and direct bond can additionally be substituted by a group having a —O—C-bond or a —O—Si-bond which cleaves upon the action of an acid;

A$_1$ is a direct bond, C$_1$-C$_{18}$alkylene, —O—, —S—, —NM$_{23}$-, —O(CO)—, —S(CO)—, —NM$_{23}$(CO)—, —SO—, —SO$_2$— or —OSO$_2$—;

A$_2$ is a direct bond, C$_1$-C$_{18}$alkylene; or is C$_2$-C$_{18}$alkylene which is interrupted by one or more C$_3$-C$_{30}$cycloalkylene, —O—, —S—, —NM$_{23}$-, —(CO)—, —O(CO)—, —S(CO)—, —NM$_{23}$(CO)—, —SO—, —SO$_2$—, —OSO$_2$— or —Ar$_2$—; optionally the radicals C$_1$-C$_{18}$alkylene and C$_2$-C$_{18}$alkylene are substituted by one or more C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or A$_2$ is C$_3$-C$_{30}$cycloalkylene, optionally interrupted by one or more —O—, —S—, —NM$_{23}$-, —(CO)—, —O(CO)—, or —NM$_{23}$(CO)—, and which is unsubstituted or substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or A$_2$ is phenylene, naphthylene, wherein these radicals optionally are substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

M$_2$ has one of the meanings of M$_1$ or is C$_2$-C$_{18}$alkanoyl; benzoyl that is unsubstituted or substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_2$ is NO$_2$; or M$_2$ is S(O)$_p$—C$_1$-C$_{18}$alkyl, S(O)$_p$—C$_6$-C$_{12}$aryl, SO$_2$O—C$_1$-C$_{18}$alkyl, SO$_2$O—C$_6$-C$_{10}$aryl, diphenyl-phosphinoyl, all of which optionally are substituted by one or more C$_1$-C$_{18}$alkyl, C$_1$-C$_8$haloalkyl, C$_3$-C$_{30}$cycloalkyl; C$_3$-C$_{30}$cycloalkyl which is interrupted by one or more —O—, —S—, —NM$_{23}$-, —O(CO)—, or —NM$_{23}$(CO)—; or are substituted by halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_1$ and M$_2$ together form a 5-, 6- or 7-membered ring which is unsubstituted or substituted by one or more C$_1$-C$_{18}$alkyl, C$_1$-C$_8$haloalkyl, C$_3$-C$_{30}$cycloalkyl;

$C_3$-$C_{30}$cycloalkyl which is interrupted by one or more —O—, —S—, —$NM_{23}$-, —O(CO)—, or —$NM_{23}$(CO)—; or is substituted by halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$; and said 5-, 6- or 7-membered ring may additionally be interrupted by $C_{1-18}$alkylene, $C_3$-$C_{30}$cycloalkylene, $C_1$-$C_8$haloalkylene, $C_2$-$C_{12}$alkenylene, $C_4$-$C_{30}$cycloalkenylene, phenylene, naphthalene, —O—, —S—, —$NM_{23}$-, —(CO)—, —O(CO)—, —$NM_{23}$(CO)—, —S(CO)—, —SO—, —$SO_2$—, or —$OSO_2$—, and to said 5-, 6- or 7-membered ring optionally are fused one or more benzo radicals;

p is 1 or 2;

X is —O(CO)$M_{24}$, —O(CO)$OM_{20}$, —O(CO)$NM_{21}M_{22}$, —$NM_{23}$(CO)$M_{24}$, —$NM_{23}$(CO)$OM_{20}$, —$OM_{20}$, —$NM_{21}M_{22}$,

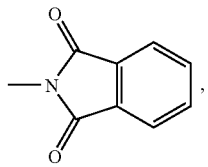

—$SM_{23}$, —$SOM_{19}$, —$SO_2M_{19}$, —$OSO_2M_{19}$, or the groups

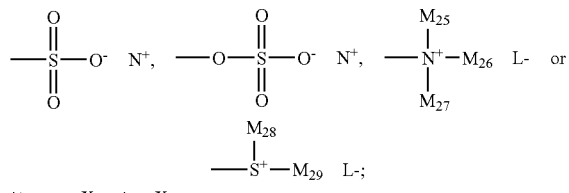

X' is —$X_1$—$A_3$—$X_2$—;

$X_1$ and $X_2$ independently of each other are —O(CO)—, —O(CO)O—, —O(CO)$NM_{23}$-, —$NM_{23}$(CO)—, —$NM_{23}$(CO)O—, —O—, —$NM_{23}$-, —S—, —SO—, —$SO_2$—, —$OSO_2$—,

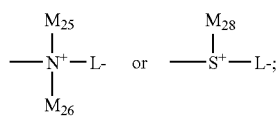

or $X_1$ and $X_2$ are a direct bond, with the proviso that $X_1$ and $X_2$ are not both simultaneously a direct bond;

$A_3$ is phenylene, naphthylene,

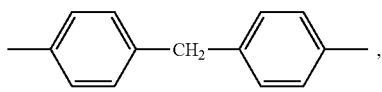

diphenylene, oxydiphenylene or

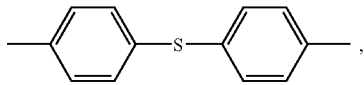

wherein these radicals are unsubstituted or substituted by one or more $C_1$-$C_{18}$alkyl, $C_1$-$C_8$haloalkyl, $C_3$-$C_{30}$cycloalkyl, halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$, or $A_3$ is a direct bond,

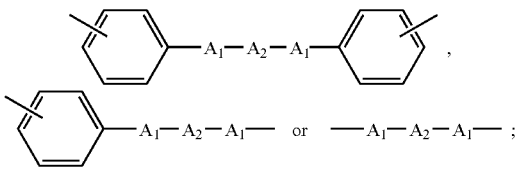

$M_3$ has one of the meanings given for $M_1$; or $M_3$ is $C_2$-$C_{18}$alkanoyl; benzoyl which optionally is substituted by one or more $C_1$-$C_{18}$alkyl, $C_1$-$C_8$haloalkyl, $C_3$-$C_{30}$cycloalkyl, halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$;

or $M_3$ is $NO_2$; or $M_3$ is S(O)$_p$—$C_1$-$C_{18}$alkyl, S(O)$_p$—$C_6$-$C_{12}$aryl, $SO_2O$—$C_1$-$C_{18}$alkyl, $SO_2O$—$C_6$-$C_{10}$aryl, diphenyl-phosphinoyl, all of which optionally are substituted by one or more $C_1$-$C_{18}$alkyl, $C_1$-$C_8$haloalkyl, $C_3$-$C_{30}$cycloalkyl; $C_3$-$C_{30}$cycloalkyl which is interrupted by one or more —O—, —S—, —$NM_{23}$-, —O(CO)—, or —$NM_{23}$(CO)—; or is substituted by halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$;

$M_4$ has one of the meaning given for $M_2$, or $M_3$ and $M_4$ together form a 5-, 6- or 7-membered ring which optionally is substituted by one or more $C_1$-$C_{18}$alkyl, $C_1$-$C_8$haloalkyl, $C_3$-$C_{30}$cycloalkyl; $C_3$-$C_{30}$cycloalkyl which is interrupted by one or more —O—, —S—, —$NM_{23}$-, —O(CO)—, or —$NM_{23}$(CO)—; or said 5-, 6- or 7-membered ring is substituted by halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$; and said 5-, 6- or 7-membered ring optionally additionally is interrupted by $C_{1-18}$alkylene, $C_3$-$C_{30}$cycloalkylene, $C_1$-$C_8$haloalkylene, $C_2$-$C_{12}$alkenylene, $C_4$-$C_{30}$cycloalkenylene, phenylene, naphthalene, —O—, —S—, —$NM_{23}$-, —(CO)—, —O(CO)—, —$NM_{23}$(CO)—, —S(CO)—, —SO—, —$SO_2$—, or —$OSO_2$—; and optionally one or more benzo radicals are fused to said 5-, 6- or 7-membered ring;

$M_5$ and $M_6$ independently of each other are hydrogen, $C_1$-$C_{18}$alkyl, $C_1$-$C_8$haloalkyl, $C_3$-$C_{30}$cycloalkyl; $C_3$-$C_{30}$cycloalkyl which is interrupted by one or more —O—, —S—, —NM$_{23}$-, —O(CO)—, or —NM$_{23}$(CO)—; or M$_5$ and M$_6$ are halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_5$ and M$_6$ together are —C(M$_{30}$)=C(M$_{31}$)-C(M$_{32}$)=C(M$_{33}$)- or —(CO)NM$_{23}$(CO)—;

G is —S—, —O—, —NM$_{23}$-, or a group of formula Z$_1$, Z$_2$, Z$_3$ or Z$_4$

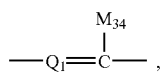
(Z$_1$)

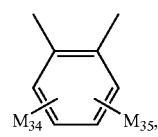
(Z$_2$)

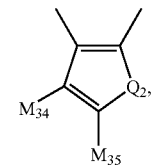
(Z$_3$)

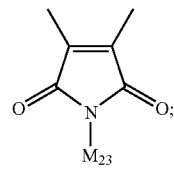
(Z$_4$)

M$_7$ when n is 1, is phenyl, naphthyl, anthracyl, phenanthryl, or heteroaryl, all of optionally are substituted by one or more C$_1$-C$_{18}$alkyl, C$_1$-C$_8$haloalkyl, C$_3$-C$_{30}$cycloalkyl; C$_3$-C$_{30}$cycloalkyl which is interrupted by one or more —O—, —S—, —NM$_{23}$-, —O(CO)— or —NM$_{23}$(CO)—; or are substituted by halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$, optionally the substituents —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$ form 5-, 6- or 7-membered rings, via the radicals M$_{19}$, M$_{20}$, M$_{21}$M$_{22}$ and/or M$_{23}$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

or M$_7$ is C$_1$-C$_{18}$alkyl; or is C$_2$-C$_{18}$alkyl which is interrupted by one or more C$_3$-C$_{30}$cycloalkylene, —O—, —S—, —NM$_{23}$-, —(CO)—, —O(CO)—, —S(CO)—, —NM$_{23}$(CO)—, —SO—, —SO$_2$—, or —OSO$_2$—; optionally the radicals C$_1$-C$_{18}$alkyl and C$_2$-C$_{18}$alkyl are substituted by one or more C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_7$ is C$_3$-C$_{30}$cycloalkyl, optionally interrupted by one or more —O—, —S—, —NM$_{23}$-, —(CO)—, —O(CO)—, or —NM$_{23}$(CO)—, and optionally substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or M$_7$ is hydrogen, C$_1$-C$_8$haloalkyl, —OM$_{20}$, —NM$_{21}$M$_{22}$, —NM$_{23}$(CO)M$_{19}$, —SM$_{23}$, C$_2$-C$_{12}$alkenyl, C$_4$-C$_{30}$cycloalkenyl, camphoryl; and M$_7$, when n is 2, is phenylene, naphthylene,

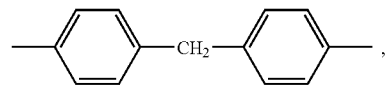

diphenylene, oxydiphenylene or

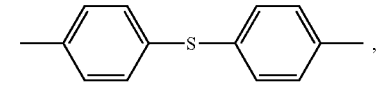

wherein these radicals are optionally substituted by one or more C$_1$-C$_{18}$alkyl, C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$, or M$_7$ is a direct bond,

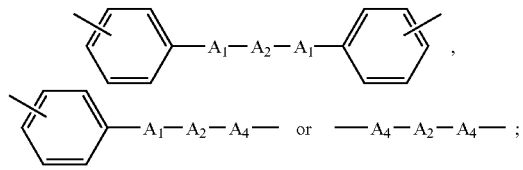

wherein all radicals M$_7$ with the exception of hydrogen and direct bond optionally additionally are substituted by a group having a —O—C-bond or a —O—Si-bond which cleaves upon the action of an acid;

A$_4$ is a direct bond, C$_1$-C$_{18}$alkylene, —O—, —S— or —NM$_{23}$-;

M$_8$ and M$_9$ independently of each other are C$_1$-C$_{18}$alkyl; or are C$_2$-C$_{18}$alkyl which is interrupted by one or more C$_3$-C$_{30}$cycloalkylene, —O—, —S—, —NM$_{23}$-, —(CO)—, —O(CO)—, —S(CO)—, —NM$_{23}$(CO)—, —SO—, —SO$_2$—, —OSO$_2$— or —Ar$_2$—; optionally the radicals C$_1$-C$_{18}$alkyl and C$_2$-C$_{18}$alkyl are substituted by one or more C$_1$-C$_8$haloalkyl, C$_3$-C$_{30}$cycloalkyl, halogen, —NO$_2$, —CN, —Ar$_1$, —(CO)M$_{19}$, —(CO)OM$_{20}$, —(CO)NM$_{21}$M$_{22}$, —O(CO)M$_{19}$, —O(CO)OM$_{20}$, —O(CO)NM$_{21}$M$_{22}$, —NM$_{23}$(CO)M$_{19}$, —NM$_{23}$(CO)OM$_{20}$, —OM$_{20}$, —NM$_{21}$M$_{22}$, —SM$_{23}$, —SOM$_{19}$, —SO$_2$M$_{19}$ and/or —OSO$_2$M$_{19}$;

or $M_8$ and $M_9$ are $C_3$-$C_{30}$cycloalkyl, optionally interrupted by one or more —O—, —S—, —$NM_{23}$-, —(CO)—, —O(CO)—, or —$NM_{23}$(CO)—, and optionally substituted by one or more $C_1$-$C_{18}$alkyl, $C_1$-$C_8$haloalkyl, $C_3$-$C_{30}$cycloalkyl, halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$;

or $M_8$ and $M_9$ are hydrogen, halogen, $C_1$-$C_8$haloalkyl, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$;

or $M_8$ and $M_9$, if appropriate, together with $C_1$-$C_4$alkylene, —O—, —S—, —$NM_{23}$-, —(CO)—, —O(CO)—, —$NM_{23}$(CO)— form a 5-, 6-, or 7-membered ring;

or $M_7$ and $M_8$, if appropriate, together with $C_1$-$C_3$alkylene, —O—, —S—, —$NM_{23}$, —(CO)—, —O(CO)—, —$NM_{23}$(CO)— form a 5-, 6-, or 7-membered ring;

$M_{10}$ has one of the meanings given for $M_7$;

$M_{11}$ is $C_1$-$C_{18}$alkyl; or $C_2$-$C_{18}$alkyl which is interrupted by one or more $C_3$-$C_{30}$cycloalkylene, —O—, —S—, —$NM_{23}$-, —(CO)—, —O(CO)—, —S(CO)—, —$NM_{23}$(CO)—, —SO—, —$SO_2$—, —$OSO_2$— or —$Ar_2$—; optionally the radicals $C_1$-$C_{18}$alkyl and $C_2$-$C_{18}$alkyl are substituted by one or more $C_1$-$C_8$haloalkyl, $C_3$-$C_{30}$cycloalkyl, halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$;

or $M_{11}$ is $C_3$-$C_{30}$cycloalkyl, optionally interrupted by one or more —O—, —S—, —$NM_{23}$-, —(CO)—, —O(CO)—, or —$NM_{23}$(CO)—, and optionally substituted by one or more $C_1$-$C_{18}$alkyl, $C_1$-$C_8$haloalkyl, $C_3$-$C_{30}$cycloalkyl, halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$; or $M_{11}$ is hydrogen, $C_1$-$C_8$haloalkyl, —$Ar_1$, —(CO)$M_{19}$, —(CO)$OM_{20}$, —(CO)$NM_{21}M_{22}$ or —$SO_2M_{19}$;

or $M_{10}$ and $M_{11}$ together form a 5-, 6- or 7-membered ring which optionally is substituted by one or more $C_1$-$C_{18}$alkyl, $C_1$-$C_8$haloalkyl, $C_3$-$C_{30}$cycloalkyl; $C_3$-$C_{30}$cycloalkyl which is interrupted by one or more —O—, —S—, —$NM_{23}$-, —O(CO)—, or —$NM_{23}$(CO)—; or said 5-, 6- or 7-membered ring is substituted by halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$; and said 5-, 6- or 7-membered ring optionally additionally is interrupted by $C_1$-$C_{12}$alkylene, $C_3$-$C_{30}$cycloalkylene, $C_1$-$C_8$haloalkylene, $C_2$-$C_{12}$alkenylene, $C_4$-$C_{30}$-cycloalkenylene, phenylene, naphthalene, —O—, —S—, —$NM_{23}$, —(CO)—, —O(CO)—, —$NM_{23}$(CO)—, —S(CO)—, —SO—, —$SO_2$—, or —$OSO_2$—; and to said 5-, 6- or 7-membered ring optionally are fused one or more benzo radicals;

$M_{12}$, $M_{13}$, $M_{14}$ and $M_{15}$ independently of each other are hydrogen, $C_1$-$C_{18}$alkyl, $C_1$-$C_8$haloalkyl, $C_3$-$C_{30}$cycloalkyl; $C_3$-$C_{30}$cycloalkyl which is interrupted by one or more —O—, —S—, —$NM_{23}$-, —O(CO)—, or —$NM_{23}$(CO)—; or $M_{12}$, $M_{13}$, $M_{14}$ and $M_{15}$ are halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$; optionally the substituents $M_{12}$, $M_{13}$, $M_{14}$ and/or $M_{15}$ form 5-, 6- or 7-membered rings or fused rings, via the radicals $M_{12}$, $M_{13}$, $M_{14}$ and/or $M_{15}$ with further substituents on the phenyl to which $M_{12}$, $M_{13}$, $M_{14}$ and $M_{15}$ are bonded, or with one of the carbon atoms of said phenyl ring;

wherein all radicals $M_{12}$, $M_{13}$, $M_{14}$ and/or $M_{15}$ with the exception of hydrogen optionally additionally are substituted by a group having a —O—C-bond or a —O—Si-bond which cleaves upon the action of an acid;

$M_{16}$, $M_{17}$ and $M_{18}$ independently of each other are hydrogen, $C_1$-$C_{18}$alkyl, $C_1$-$C_8$haloalkyl, $C_3$-$C_{30}$cycloalkyl; $C_3$-$C_{30}$cycloalkyl which is interrupted by one or more —O—, —S—, —$NM_{23}$-, —O(CO)—, or —$NM_{23}$(CO)—; or $M_{16}$, $M_{17}$ and $M_{18}$ are halogen, —$NO_2$, —CN, —$Ar_1$, —(CO)$M_{19}$, —(CO)$OM_{20}$, —(CO)$NM_{21}M_{22}$, —O(CO)$M_{19}$, —O(CO)$OM_{20}$, —O(CO)$NM_{21}M_{22}$, —$NM_{23}$(CO)$M_{19}$, —$NM_{23}$(CO)$OM_{20}$, —$OM_{20}$, —$NM_{21}M_{22}$, —$SM_{23}$, —$SOM_{19}$, —$SO_2M_{19}$ and/or —$OSO_2M_{19}$, optionally the substituents $M_{16}$, $M_{17}$, and/or $M_{18}$ form 5-, 6- or 7-membered rings or fused rings, via the radicals $M_{16}$, $M_{17}$, and/or $M_{18}$ with further substituents on the phenyl ring to which $M_{16}$, $M_{17}$ and $M_{18}$ are bonded or with one of the carbon atoms of said phenyl ring;

wherein all radicals $M_{16}$, $M_{17}$, and/or $M_{18}$ with the exception of hydrogen optionally additionally are substituted by a group having a —O—C-bond or a —O—Si-bond which cleaves upon the action of an acid;

$M_{19}$ is phenyl, naphthyl, $C_3$-$C_{30}$cycloalkyl, $C_1$-$C_{18}$alkyl, $C_1$-$C_8$haloalkyl, $C_2$-$C_{12}$alkenyl, $C_4$-$C_{30}$cycloalkenyl; or is $C_2$-$C_{18}$alkyl which is interrupted by one or more —O—; or is $C_3$-$C_{30}$cycloalkyl which is interrupted by one or more —O—, —S—, —$NM_{23}$-, —O(CO)—, or —$NM_{23}$(CO)—;

all of which optionally are substituted by one or more $Ar_1$, OH, $C_1$-$C_{18}$alkyl, $C_1$-$C_8$-haloalkyl, $C_3$-$C_{30}$cycloalkyl, halogen, —$NO_2$, —CN, $C_1$-$C_{12}$alkoxy, phenoxy, phenoxycarbonyl, phenylthio, phenylthiocarbonyl, —$NM_{21}M_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy;

or $M_{19}$ is hydrogen;

$M_{20}$ is phenyl, naphthyl, $C_3$-$C_{30}$cycloalkyl, $C_1$-$C_{18}$alkyl, $C_1$-$C_8$haloalkyl, $C_2$-$C_{12}$alkenyl, $C_4$-$C_{30}$cycloalkenyl; or is $C_2$-$C_{18}$alkyl which is interrupted by one or more —O—; or is $C_3$-$C_{30}$cycloalkyl which is interrupted by one or more —O—, —S—, —$NM_{23}$-, —O(CO)— or —$NM_{23}$(CO)—; or is $C_2$-$C_{18}$alkanoyl, or is benzoyl, or is $C_1$-$C_{18}$alkylsulfonyl, all of which optionally are substituted by one or more $Ar_1$, OH, $C_1$-$C_{18}$alkyl, $C_1$-$C_8$-haloalkyl, $C_3$-$C_{30}$cycloalkyl, halogen, —$NO_2$, —CN, $C_1$-$C_{12}$alkoxy, phenoxy, phenoxycarbonyl, phenylthio, phenylthiocarbonyl, —$NM_{21}M_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy;

or $M_{20}$ is hydrogen, phenylsulfonyl, (4-methylphenyl)sulfonyl, naphthylsulfonyl, anthracylsulfonyl or phenanthrylsulfonyl;

$M_{21}$, $M_{22}$ and $M_{23}$ independently of each other are phenyl, naphthyl, $C_3$-$C_{30}$cycloalkyl, $C_1$-$C_{18}$alkyl, $C_1$-$C_8$haloalkyl, $C_2$-$C_{12}$alkenyl, $C_4$-$C_{30}$cycloalkenyl; or are $C_2$-$C_{18}$alkyl which is interrupted by one or more —O—; or are $C_3$-$C_{30}$cycloalkyl which is interrupted by one or more —O—, —S—, —NM 23-, —O(CO)—, or —NM$_{23}$(CO)—; or are $C_2$-$C_{18}$alkanoyl, benzoyl or $C_1$-$C_{18}$alkylsulfonyl, all of which optionally are substituted by one or more $Ar_1$, OH, $C_1$-$C_{18}$alkyl, $C_1$-$C_8$haloalkyl, $C_3$-$C_{30}$cycloalkyl, halogen, —NO$_2$, —CN, $C_1$-$C_{12}$alkoxy, phenoxy, phenoxycarbonyl, phenylthio, phenylthiocarbonyl, —NM$_{21}$M$_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)-sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy;

or $M_{21}$, $M_{22}$ and $M_{23}$ independently of each other are hydrogen, phenylsulfonyl, (4-methylphenyl)sulfonyl, naphthylsulfonyl, anthracylsulfonyl or phenanthrylsulfonyl;

or $M_{21}$ and $M_{22}$, together with the nitrogen atom to which they are attached, form a 5-, 6- or 7-membered ring which optionally is interrupted by —O— or by —NM$_{23}$-;

$M_{24}$ is phenyl, naphthyl, $C_3$-$C_{30}$cycloalkyl, $C_1$-$C_{18}$alkyl, $C_1$-$C_8$haloalkyl, $C_4$-$C_{30}$cycloalkenyl; or is $C_2$-$C_{18}$alkyl which is interrupted by one or more —O—, or is $C_3$-$C_{30}$cycloalkyl which is interrupted by one or more —O—, —S—, —NM$_{23}$-, —O(CO)—, or —NM$_{23}$(CO)—;

all of which are unsubstituted or substituted by one or more $Ar_1$, OH, $C_1$-$C_{18}$alkyl, $C_1$-$C_8$haloalkyl, $C_3$-$C_{30}$cycloalkyl, halogen, —NO$_2$, —CN, $C_1$-$C_{12}$alkoxy, phenoxy, phenoxycarbonyl, phenylthio, phenylthiocarbonyl, —NM$_{21}$M$_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy;

or $M_{24}$ is hydrogen;

or $M_{23}$ and $M_{24}$ together with the N-atom to which they are attached form a 5-, 6- or 7-membered ring which optionally is interrupted by —O— and which additionally optionally is fused with one or more benzo rings;

$M_{25}$, $M_{26}$ and $M_{27}$ independently of each other are hydrogen; or are phenyl or naphthyl, both of which optionally are substituted by one or more $Ar_1$, OH, $C_1$-$C_{18}$alkyl, $C_1$-$C_8$haloalkyl, $C_3$-$C_{30}$cycloalkyl, halogen, —NO$_2$, —CN, $C_1$-$C_{12}$alkoxy, phenoxy, phenoxycarbonyl, phenylthio, phenylthiocarbonyl, —NM$_{21}$M$_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)-sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy; or $M_{25}$, $M_{26}$ and $M_{27}$ are $C_3$-$C_{18}$alkenyl or $C_3$-$C_{18}$alkynyl; or $M_{25}$, $M_{26}$ and $M_{27}$ are $C_1$-$C_{18}$alkyl, $C_2$-$C_{18}$alkyl which is interrupted by one or more —O—, and wherein the radicals $C_1$-$C_{18}$alkyl and $C_2$-$C_{18}$alkyl are optionally substituted by one or more $Ar_1$, OH, $C_1$-$C_{18}$alkyl, $C_1$-$C_8$haloalkyl, $C_3$-$C_{30}$cycloalkyl, halogen, —NO$_2$, —CN, $C_1$-$C_{12}$alkoxy, phenoxy, phenoxycarbonyl, phenylthio, phenylthiocarbonyl, —NM$_{21}$M$_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)-sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy; or $M_{25}$ and $M_{26}$, if appropriate together with $C_1$-$C_2$alkylene, —O—, —S—, or —CO—, form a fused ring; or $M_{25}$, $M_{26}$ and $M_{27}$, if appropriate together with $C_1$-$C_2$alkylene, —O—, —S—, or —CO—, form a 5-, 6- or 7-membered ring; or $M_{25}$, $M_{26}$ and $M_{27}$ together with the N$^+$-atom to which they are bonded form a group

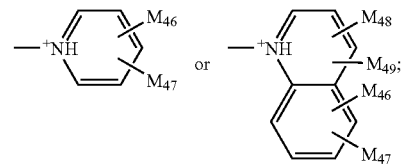

$M_{28}$ and $M_{29}$ independently of each other are phenyl which optionally is substituted by one or more $Ar_1$, OH, $C_1$-$C_{18}$alkyl, $C_1$-$C_8$haloalkyl, $C_3$-$C_{30}$cycloalkyl, halogen, —NO$_2$, —CN, $C_1$-$C_{12}$alkoxy, phenoxy, phenoxycarbonyl, phenylthio, phenylthiocarbonyl, —NM$_{21}$M$_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy; or $M_{28}$ and $M_{29}$ independently of each other are $C_1$-$C_{18}$alkyl, $C_2$-$C_{18}$alkyl which is interrupted by one or more —O—, and wherein the radicals $C_1$-$C_{18}$alkyl and $C_2$-$C_{18}$alkyl are optionally substituted by one or more $Ar_1$, OH, $C_1$-$C_{18}$alkyl, $C_1$-$C_8$haloalkyl, $C_3$-$C_{30}$cycloalkyl, halogen, —NO$_2$, —CN, $C_1$-$C_{12}$alkoxy, phenoxy, phenoxycarbonyl, phenylthio, phenylthiocarbonyl, —NM$_{21}$M$_{22}$, $C_1$-$C_{12}$alkylthio, $C_2$-$C_{12}$alkoxycarbonyl, $C_2$-$C_8$haloalkanoyl, halobenzoyl, $C_1$-$C_{12}$alkylsulfonyl, phenylsulfonyl, (4-methylphenyl)sulfonyl, $C_1$-$C_{12}$alkylsulfonyloxy, phenylsulfonyloxy, (4-methylphenyl)sulfonyloxy, $C_2$-$C_{12}$alkanoyl, $C_2$-$C_{12}$alkanoyloxy, benzoyl and/or by benzoyloxy; or $M_{28}$ and $M_{29}$, if appropriate together with $C_1$-$C_2$alkylene, —O—, —S—, or —CO—, form a fused ring; or $M_{28}$ and $M_{29}$, if appropriate together with $C_1$-$C_2$alkylene, —O—, —S—, or —CO—, form a 5-, 6- or 7-membered ring;

$M_{30}$, $M_{31}$, $M_{32}$ and $M_{33}$ are independently of each other hydrogen, halogen, $C_1$-$C_{18}$alkyl, $C_1$-$C_{18}$alkoxy, $C_1$-$C_8$haloalkyl, CN, NO$_2$, $C_2$-$C_{18}$alkanoyl, benzoyl, phenyl, —S-phenyl, OM$_{20}$, SM$_{23}$, NM$_{21}$M$_{22}$, $C_2$-$C_6$alkoxycarbonyl, phenoxycarbonyl, S(O)$_p$C$_1$-$C_{18}$alkyl, unsubstituted or $C_1$-$C_{18}$alkyl-substituted S(O)$_p$—C$_6$-$C_{12}$aryl, SO$_2$O—C$_1$-$C_{18}$alkyl, SO$_2$O—C$_6$-$C_{10}$aryl or NHCONH$_2$;

$M_{34}$ and $M_{35}$ independently of each other have one of the meanings given for $M_5$;

or $M_{34}$ and $M_{35}$ together are $-CO-NM_{23}CO-$; or $M_{34}$ and $M_{35}$ together are $-C(M_{30})=C(M_{31})-C(M_{32})=C(M_{33})-$;

$Ar_1$ is phenyl, naphthyl, anthracyl, phenanthryl, or heteroaryl, all of which optionally are substituted by one or more $C_1-C_{18}$alkyl, $C_1-C_8$haloalkyl, $C_3-C_{30}$cycloalkyl; $C_3-C_{30}$cycloalkyl which is interrupted by one or more $-O-$, $-S-$, $-NM_{23}-$, $-O(CO)-$, or $-NM_{23}(CO)-$; or are substituted by halogen, $-NO_2$, $-CN$, phenyl, $-(CO)M_{19}$, $-(CO)OM_{20}$, $-(CO)NM_{21}M_{22}$, $-O(CO)M_{19}$, $-O(CO)OM_{20}$, $-O(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$, optionally the substituents $-(CO)M_{19}$, $-(CO)OM_{20}$, $-(CO)NM_{21}M_{22}$, $-O(CO)M_{19}$, $-O(CO)OM_{20}$, $-O(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$ form 5-, 6- or 7-membered rings, via the radicals $M_{19}$, $M_{20}$, $M_{21}M_{22}$ and/or $M_{23}$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

$Ar_2$ is phenylene, naphthylene, $$-\!\!\!\!\phantom{x}\!\!\!\!\langle\text{phenyl}\rangle\!-\!CH_2\!-\!\langle\text{phenyl}\rangle\!\!\!\!\phantom{x}\!\!\!\!-,$$

diphenylene, oxydiphenylene or $$-\!\!\!\!\phantom{x}\!\!\!\!\langle\text{phenyl}\rangle\!-\!S\!-\!\langle\text{phenyl}\rangle\!\!\!\!\phantom{x}\!\!\!\!-,$$

wherein these radicals optionally are substituted by one or more $C_1-C_{18}$alkyl, $C_1-C_8$haloalkyl, $C_3-C_{30}$cycloalkyl, halogen, $-NO_2$, $-CN$, $-Ar_1$, $-(CO)M_{19}$, $-(CO)OM_{20}$, $-(CO)NM_{21}M_{22}$, $-O(CO)M_{19}$, $-O(CO)OM_{20}$, $-O(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$, optionally the substituents $-(CO)M_{19}$, $-(CO)OM_{20}$, $-(CO)NM_{21}M_{22}$, $-O(CO)M_{19}$, $-O(CO)OM_{20}$, $-(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$ form 5-, 6- or 7-membered rings, via the radicals $M_{19}$, $M_{20}$, $M_{21}M_{22}$ and/or $M_{23}$, with further substituents on these radicals or with one of the carbon atoms of these radicals;

$N^+$ is $$M_{39}\!-\!\overset{\overset{M_{36}}{|}}{\underset{\underset{M_{38}}{|}}{N^+}}\!-\!M_{37},\quad M_{40}\!-\!\overset{\overset{M_{41}}{|}}{S^+}\!-\!M_{42},$$

$M_{43}$-$I^+$-$M_{44}$, $Li^+$, $Na^+$, $K^+$, $Cs^+$, $\frac{1}{2}Mg^{2+}$, $\frac{1}{2}Ca^{2+}$ or $\frac{1}{2}Ba^{2+}$;

$L^-$ is $F^-$, $Cl^-$, $Br^-$, $I^-$, $HSO_4^-$, $\frac{1}{2}SO_4^{2-}$, $NO_3^-$, $$M_{45}\!-\!\overset{\overset{O}{\|}}{\underset{\underset{O}{\|}}{S}}\!-\!O^-,\quad M_{45}\!-\!O\!-\!\overset{\overset{O}{\|}}{\underset{\underset{O}{\|}}{S}}\!-\!O^-,\quad M_{45}\!-\!\overset{\overset{O}{\|}}{C}\!-\!O^-,$$

$$M_{45}\!-\!\overset{\overset{M_{45}}{|}}{\underset{\underset{M_{45}}{|}}{B}}\!-\!M_{45},$$

$ClO_4^-$, $BF_4^-$, $PF_6^-$, $AsF_6^-$, $SbF_6^-$, $(M_{50}SO_2)_3C^-$ or $(M_{50}SO_2)_2N^-$;

$M_{36}$, $M_{37}$, $M_{38}$ and $M_{39}$ have one of the meanings given for $M_{25}$, $M_{26}$ and $M_{27}$;

$M_{40}$, $M_{41}$, and $M_{42}$ have one of the meanings given for $M_{28}$ and $M_{29}$;

$M_{43}$ and $M_{44}$ independently of each other are phenyl, which optionally is substituted by one or more $Ar_1$, OH, $C_1-C_{18}$alkyl, $C_1-C_8$haloalkyl, $C_3-C_{30}$cycloalkyl, halogen, $-NO_2$, $-CN$, $C_1-C_{12}$alkoxy, phenoxy, phenoxycarbonyl, phenylthio, phenylthiocarbonyl, $-NM_{21}M_{22}$, $C_1-C_{12}$alkylthio, $C_2-C_{12}$alkoxycarbonyl, $C_2-C_8$ haloalkanoyl, halobenzoyl, $C_1-C_{12}$alkylsulfonyl, phenylsulfonyl, (4-methylphenyl)sulfonyl, $C_1-C_{12}$alkylsulfonyloxy, phenylsulfonyloxy, (4-methylphenyl)sulfonyloxy, $C_2-C_{12}$alkanoyl, $C_2-C_{12}$alkanoyloxy, benzoyl and/or by benzoyloxy; or $M_{43}$ and $M_{44}$, if appropriate together with $C_1-C_2$alkylene, $-O-$, $-S-$, or $-CO-$, form a fused ring;

$M_{45}$ is $C_1-C_{18}$alkyl, $C_1-C_8$haloalkyl, camphoryl, phenyl-$C_1-C_3$alkyl, $C_3-C_{30}$cycloalkyl, $C_4-C_{30}$cycloalkenyl, phenyl, naphthyl, anthracyl or phenanthryl; all of which optionally are substituted by one or more $C_1-C_{18}$alkyl, $C_1-C_8$haloalkyl, $C_3-C_{30}$cycloalkyl, halogen, $-NO_2$, $-CN$, $-Ar_1$, $-(CO)M_{19}$, $-(CO)OM_{20}$, $-(CO)NM_{21}M_{22}$, $-O(CO)M_{19}$, $-O(CO)OM_{20}$, $-O(CO)NM_{21}M_{22}$, $-NM_{23}(CO)M_{19}$, $-NM_{23}(CO)OM_{20}$, $-OM_{20}$, $-NM_{21}M_{22}$, $-SM_{23}$, $-SOM_{19}$, $-SO_2M_{19}$ and/or $-OSO_2M_{19}$;

$M_{46}$ and $M_{47}$ independently of one another have one of the meanings given for $M_5$;

or $M_{46}$ and $M_{47}$ together are $-CO-NM_{23}-CO-$ or $-C(M_{30})=C(M_{31})-C(M_{32})=C(M_{33})-$;

$M_{48}$ and $M_{49}$ independently of one another have on of the meanings given for $M_5$, or $M_{48}$ and $M_{49}$ together are $-CO-NM_{23}-CO-$ or $-C(M_{30})=C(M_{31})-C(M_{32})=C(M_{33})-$;

$M_{50}$ is $C_1-C_8$-perfluoroalkyl;

$Q_1$ is $-CM_{35}-$ or $-N-$; and $Q_2$ is $-CH_2-$, $-S-$, $-O-$ or $-NM_{23}-$.

It is especially preferred when the photolatent acid is selected from the group consisting of (a)

$$H_3C\!-\!\langle\text{phenyl}\rangle\!-\!\underset{\underset{CF_3}{|}}{C}\!=\!N\!-\!O\!-\!\overset{\overset{O}{\|}}{\underset{\underset{O}{\|}}{S}}\!-\!(CH_2)_2\!-\!O\!-\!CH_3$$

2,2,2-trifluoro-1-p-tolyl-ethanone oxime 2-methoxyethanesulfonate (b)
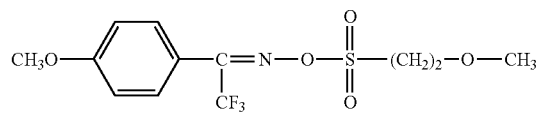

2,2,2-trifluoro-1-(4-methoxyphenyl)-ethanone oxime 2-methoxyethanesulfonate (c)
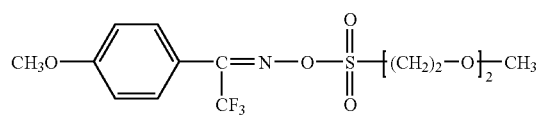

2,2,2-trifluoro-1-(4-methoxyphenyl)-ethanone oxime 2-(2-methoxy-ethoxy)-ethanesulfonate (d)
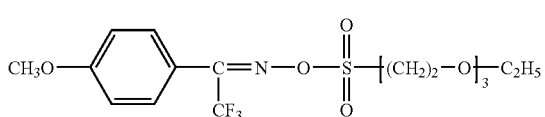

2,2,2-trifluoro-1-(4-methoxyphenyl)-ethanone oxime 2-{2-(2-ethoxy-ethoxy)-ethoxy}-ethanesulfonate (e)
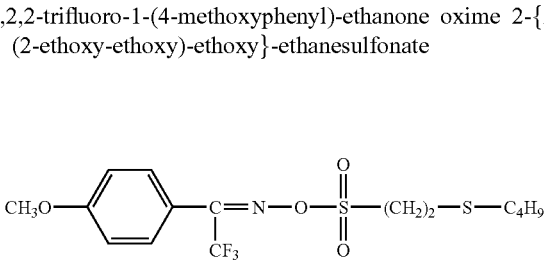

2,2,2-trifluoro-1-(4-methoxyphenyl)-ethanone oxime 2-(n-butylthio)-ethanesulfonate (f)
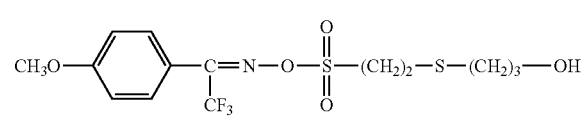

2,2,2-trifluoro-1-(4-methoxyphenyl)-ethanone oxime 2-(3-hydroxypropylthio)-ethanesulfonate (g)
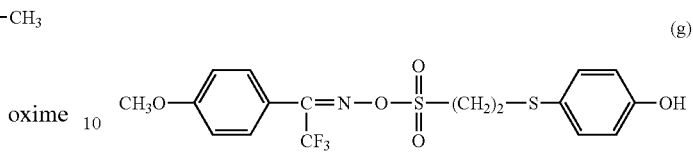

2,2,2-trifluoro-1-(4-methoxyphenyl)-ethanone oxime 2-(p-hydroxyphenylthio)-ethanesulfonate (h)
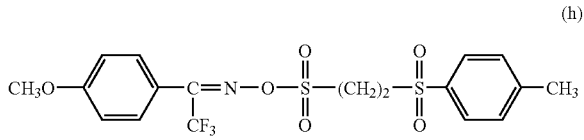

2,2,2-trifluoro-1-(4-methoxyphenyl)-ethanone oxime 2-(p-toluenesulfonyl)-ethanesulfonate (i)
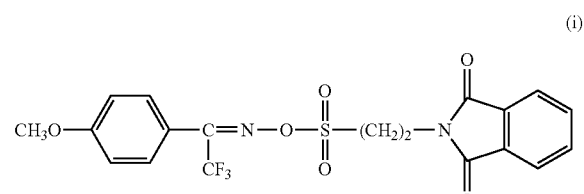

2,2,2-trifluoro-1-(4-methoxyphenyl)-ethanone oxime 2-(1,3-dioxo-1,3-dihydro-isoindol-2-yl)-ethanesulfonate (j)
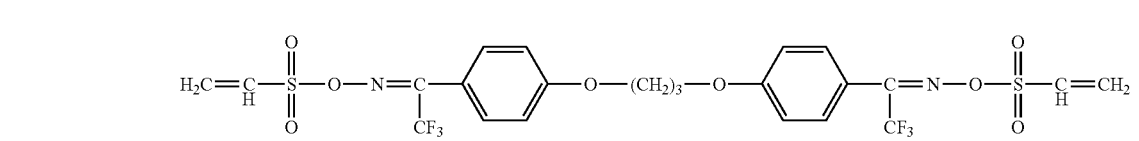

2,2,2-Trifluoro-1-(4-{3-[4-(2,2,2-trifluoro-1-vinyl sulfonyloxyimino-ethyl)-phenoxy]-propoxy}-phenyl)-ethanone oxime vinylsulfonate (k)
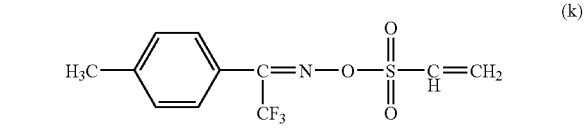

2,2,2-trifluoro-1-p-tolyl-ethanone oxime vinylsulfonate

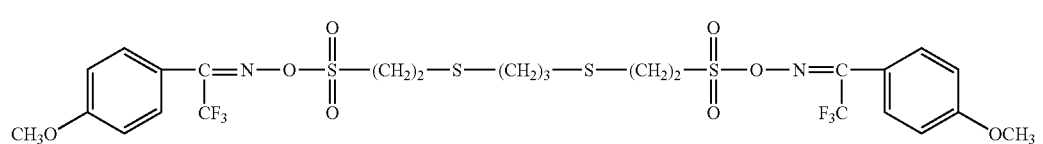

(l)

bis[2,2,2-trifluoro-1-(4-methoxyphenyl)-ethanone oxime]3,7-dithianonane-1,9-disulfonate N-(2-cyclohexylsulfanyl-ethanesulfonyloxy)-5-norbornene-2,3-dicarboximide

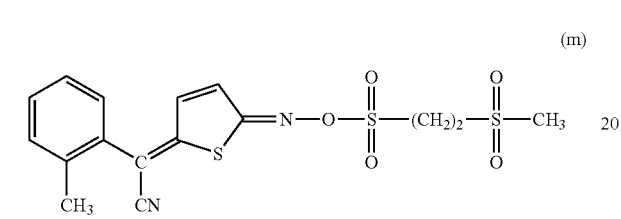

(m)

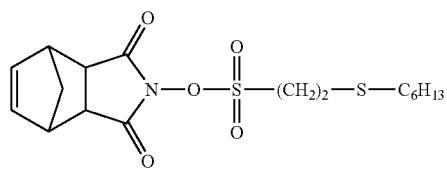

(q)

5-{2-(methanesulfonyl)-ethanesulfoxy}-imino-5H-thiophen-2-ylidene-o-tolyl-acetonitrile N-(2-hexylsulfanyl-ethanesulfonyloxy)-5-norbornene-2,3-dicarboximide

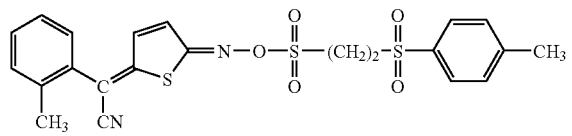

(n)

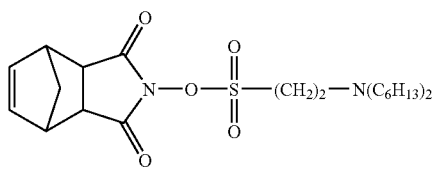

(r)

5-{2-(p-toluenesulfonyl)-ethanesulfoxy}-imino-5H-thiophen-2-ylidene-o-tolyl-acetonitrile N-(2-di-n-hexylamino-ethanesulfonyloxy)-5-norbornene-2,3-dicarboximide

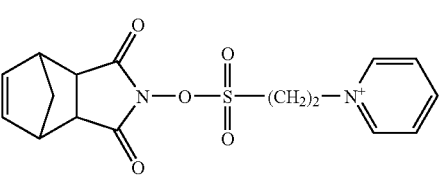

(s)

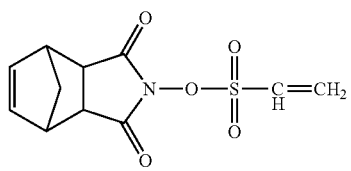

(o)

N-(ethenesulfonyloxy)-5-norbornene-2,3-dicarboximide

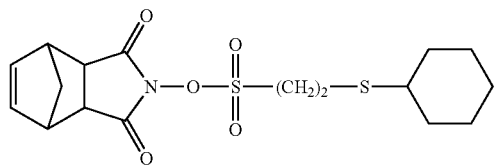

(p)

1-[2-(3,5-dioxo-4-aza-tricyclo[5.2.1.0$^{2,6}$]dec-8-en-4-yloxysulfonyl)-ethyl]-pyridinium nonafluorobutane-1-sulfonate.

The aforementioned sulfonate derivatives can also be used together with other, known photolatent acids, for example, onium salts, 6-nitrobenzylsulfonates, bis-sulfonyl diazomethane compounds, cyano group-containing oxime-sulfonate compounds, etc. These photolatent acids can also be used instead of the aforementioned sulfonate derivatives. Examples of known photolatent acids are described in U.S. Pat. No. 5,731,364, U.S. Pat. No. 5,800,964, EP 704762, U.S. Pat. No. 5,468,589, U.S. Pat. No. 5,558,971, U.S. Pat. No. 5,558,976, U.S. Pat. No. 6,004,724, GB 2348644 and particularly in EP 794457 and EP 795786.

If a mixture of photolatent acids is used in the TTI according to the invention, the weight ratio of sulfonate derivatives of formula Ia, Ib, IIa, IIb, IIIa, IIIb, IVa, IVb, Va, Vb or VIa to the other photolatent acid in the mixture is preferably from 1:99 to 99:1.

Examples of photolatent acids which are suitable to be used in admixture with the compounds of formula Ia, Ib, IIa, IIb, IIIa, IIIb, IVa, IVb, Va, Vb or VIa are (1) Onium Salt Compounds, for Example, iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxyphenyl)benzylmethylsulfonium toluenesulfonate and the like. Particularly preferred are triphenylsulfonium triflate, diphenyliodonium hexafluoroantimonate.

(2) Halogen-Containing Compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methoxyphenyl-bis(trichloromethyl)-s-triazine, naphthyl-bis(trichloromethyl)-s-triazine and the like; 1,1-bis(4-chlorophenyl)-2,2,2-trichloroethane; and the like.

(3) Sulfone Compounds, for Example

β-ketosulfones, β-sulfonylsulfones and their α-diazo derivatives and the like. Preferred are phenacyl phenylsulfone, mesitylphenacylsulfone, bis(phenylsulfonyl)methane, bis(phenylsulfonyl)diazomethane.

(4) Sulfonate Compounds, for Example alkylsulfonic acid esters, haloalkylsulfonic acid esters, arylsulfonic acid esters, iminosulfonates, imidosulfonates and the like. Preferred imidosulfonate compounds are, for example, N-(trifluoromethylsulfonyloxy)succinimide, N-(trifluoromethylsulfonyloxy)phthalimide, N-(trifluoromethylsulfonyloxy)naphthyl imide, N-(trifluoromethylsulfonyloxy)diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide, N-(camphanylsulfonyloxy)succinimide, N-(camphanylsulfonyloxy)naphthalimide, N-(camphanylsulfonyloxy)naphthylimide, N-(camphanylsulfonyloxy)diphenylmaleimide, N-(camphanylsulfonyloxy)bicyclo-[2,2,1]-hept-5-ene-2,3-dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-[2,2,1]-heptan-5,6-oxy-2,3-dicarboximide, N-(4-methylphenylsulfonyloxy)succinimide, N-(4-methylphenylsulfonyloxy)naphthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2,2,1]-hept-5-ene-2,3-dicarboximide, N-(4-methylphenylsulfonyloxy)-7-oxabicyclo-[2,2,1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy)succinimide, N-(2-trifluoromethylphenylsulfonyloxy)naphthylimide, N-(2-trifluoromethylphenylsulfonyloxy)diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like.

Other suitable sulfonate compounds preferably are, for example, benzoin tosylate, pyrogallol tristriflate, pyrogallolomethanesulfonic acid triester, nitrobenzyl-9,10-diethoxyanthracene-2-sulfonate, o-(4-toluene-sulfonyloxyimino)-benzyl cyamide, o-(4-toluene-sulfonyloxyimino)-4-methoxybenzyl cyamide, o-(4-toluene-sulfonyloxyimino)-2-thienylmethyl cyamide, o-(methanesulfonyloxyimino)-1-cyclohexenylacetonitrile, o-(butylsulfonyloxyimino)-1-cyclopentenylacetonitrile, (4-methylsulfonyloxyimino-cyclohexa-2,5-dienylidene)-phenyl-acetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-propylsulfonyloxyimino-5H-thiophen-2-ylidene)-(2-methylphenyl)-acetonitrile, (5-(p-toluenesulfonyloxyimino)-5H-thiophen-2-ylidene)-(2-methylphenyl)-acetonitrile, (5-(10-camphorsulfonyloxyimino)-5H-thiophen-2-ylidene)-(2-methylphenyl)-acetonitrile, (5-methylsulfonyloxyimino-5H-thiophen-2-ylidene)-(2-chlorophenyl)-acetonitrile, 2,2,2-trifluoro-1-{4-(3-[4-{2,2,2-trifluoro-1-(1-propanesulfonyloxyimino)-ethyl}-phenoxy]-propoxy)-phenyl}-ethanone oxime 1-propanesulfonate, 2,2,2-trifluoro-1-{4-(3-[4-{2,2,2-trifluoro-1-(1-p-toluenesulfonyloxyimino)-ethyl}-phenoxy]-propoxy)-phenyl}-ethanone oxime 1-p-toluenesulfonate and the like.

(5) Quinonediazide Compounds, for Example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly)hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'-tetrahydroxybenzophenone 2,2',3,4,4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxyphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-tridroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly)hydroxyphenylflavans such as 2,4,4-trimethyl-2',4',7-trihydroxy-2-phenylflavan, 2,4,4-trimethyl-2',4',5',6,7-pentahydroxy-2-phenylflavan and the like.

Usually, for the application to a substrate (preferably via inkjet), the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the sulfonate derivatives represented by formulae Ia, Ib, IIa, IIb, IIIa, IIIb, IVa, IVb, Va, Vb or VIa have good compatibility therewith and better solubility therein.

When a photolatent acid is employed for acidification to activate the azo coupling based time temperature indicator, it is necessary to convert the photolatent acid into an active acid catalyst. Accordingly, the method for printing a substrate optionally includes a modified step (b) that further comprises the conversion of the photolatent acid into an active acid catalyst by irradiation with short-wave light of wavelengths between 150 nm and 1500 nm, preferably between 250 nm and 450 nm.

After printing and/or activation, the time temperature indicator is, if necessary, provided with a protector which prevents the renewed or continued photo-induced conversion of the photolatent acid into an active acid catalyst. Such a protector may be a protective coating (overprint varnish) or a laminate that comprises a filter which, by filtering out certain wavelength ranges, is intended to prevent undesirable renewed or ongoing activation as described hereinbefore after the time-temperature clock has started.

In another embodiment, the invention also relates to a printing ink, printing ink concentrate or an ink-jet ink comprising at least one component of the above-described time temperature indicator being selected from the group consisting of the capped diazonium component, the coupling component and the photolatent acid, advantageously in a concentration of from 0.01 to 75% by weight, preferably from 1 to 50% by weight, especially from 5 to 40% by weight, more especially from 10 to 25% by weight, based on the total weight of the printing ink or printing ink concentrate. It can be used, for example, for electrophotography, intaglio printing, flexographic printing, screen printing, offset printing or letterpress printing.

The printing ink is, for example, a liquid or paste-form dispersion comprising colorant (indicator), binder and optionally solvent and/or optionally water and additives. In a liquid printing ink, the binder and, where applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

The printing inks can be used, for example, for electrophotography, intaglio printing, flexographic printing, screen printing, offset printing, lithography or letterpress printing. Suitable printing inks are both solvent-based printing inks and water-based printing inks.

Of interest are, for example, printing inks based on aqueous acrylates. Such inks are to be understood as including polymers or copolymers that are obtained by polymerisation of at least one monomer containing a group

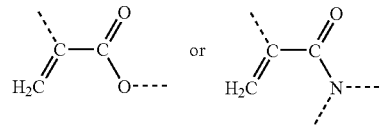

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclohexanone, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry oxidatively.

The printing inks are dried in a known manner customary in the art, optionally with heating of the coating.

A suitable aqueous printing ink composition comprises, for example, an indicator, a dispersant and a binder.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids.

The arylsulfonic acid/formaldehyde condensation products are obtainable, for example, by sulfonation of aromatic compounds, such as naphthalene itself or naphthalene-containing mixtures, and subsequent condensation of the resulting arylsulfonic acids with formaldehyde. Such dispersants are known and are described, for example, in U.S. Pat. No. 5,186,846 und DE-A-197 27 767. Suitable oxalkylated phenols are likewise known and are described, for example, in U.S. Pat. No. 4,218,218 und DE-A-197 27 767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol. It is also possible, for example, to use polymeric acids which act both as dispersants and as binders.

Examples of suitable binder components that may be mentioned include acrylate-group-containing, vinyl-group-containing and/or epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP-A-704 469, EP-A-12 339). Furthermore, in order to obtain the desired viscosity, the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary in the printing and coating industries, for example preservatives (such as glutaric dialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally $\leq$1% by weight, based on the weight of the preparation.

The printing inks may also, for example, comprise solubilisers, e.g. $\epsilon$-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

Substrate materials that may be mentioned include, for example:
cellulosic materials, such as paper, paperboard, cardboard, which may also be varnished or have some other coating,
metallic materials, such as foils, sheets or workpieces of aluminium, iron, copper, silver, gold, zinc or alloys of those metals, which may be varnished or have some other coating,
silicate materials, such as glass, china and ceramics, which may likewise be coated,
polymeric materials of all kinds, such as polystyrene, polyamides, polyester, polyethylene, polypropylene, melamine resins, polyacrylates, polyacrylonitrile, polyurethanes, polycarbonates, polyvinyl chloride and corresponding copolymers and block copolymers,
textile materials, knitted goods, woven goods, non-wovens and made-up goods of polyester, modified polyester, polyester blends, cellulosic materials, such as cotton, cotton blends, jute, flax, hemp and ramie, viscose, wool, silk, polyamide, polyamide blends, polyacrylonitrile, triacetate, acetate, polycarbonate, polypropylene, polyvinyl chloride, polyester microfibres and glass fibre fabrics,
foodstuffs and cosmetics.

Especially suitable substrates are e.g. paper, coated paper, cardboard and plastic or metal foils, such as aluminium foils.

Preference is given to printing processes wherein aqueous printing inks are used.

The printing of the substrate is preferably effected by means of continuous or dropwise ink-jet printing. The present invention relates also to non-aqueous or aqueous ink-jet inks which comprise at least one component of the above-described time temperature indicator with chromic properties based on an azo coupling reaction between a capped diazonium component and a coupling component.

The inks may be non-aqueous inks which consist of a solution of the TTI in an organic solvent or a mixture of organic solvents. Examples of solvents that can be used for this purpose are alkyl carbitols, alkyl cellosolves, dialkylformamides, dialkylacetamides, alcohols, acetone, methyl ethyl ketone, diethyl ketone, methyl isobutyl ketone, diisopropyl ketone, dibutyl ketone, dioxane, ethyl butyrate, ethyl isovalerate, diethyl malonate, diethyl succinate, butyl acetate, triethyl phosphate, ethyl glycol acetate, toluene, xylene, Tetralin or petroleum ether fractions. Examples of solid waxes as solvents that, as ink vehicles, have to be heated first, are stearic or palmitic acid.

The inks preferably comprise a total content of indicators of from 1 to 35% by weight, especially from 1 to 30% by weight and preferably from 1 to 20% by weight, based on the total weight of the ink. As lower limit, a limit of 1.5% by weight, especially 2% by weight and more especially 3% by weight, is preferred.

The inks may comprise water-miscible organic solvents, for example $C_1$-$C_4$alcohols, e.g. methanol, ethanol, n-propanol, isopropanol, n-butanol, sec-butanol, tert-butanol or iso-butanol; amides, e.g. dimethylformamide or dimethylacetamide; ketones or ketone alcohols, e.g. acetone, diacetone alcohol; ethers, e.g. tetrahydrofuran or dioxane; nitrogen-containing heterocyclic compounds, e.g. N-methyl-2-pyrrolidone or 1,3-dimethyl-2-imidazolidone, polyalkylene glycols, e.g. polyethylene glycol, or polypropylene glycol; $C_2$-$C_6$alkylene glycols and thioglycols, e.g. ethylene glycol, propylene glycol, butylene glycol, triethylene glycol, thiodiglycol, hexylene glycol and diethylene glycol; further polyols, e.g. glycerol or 1,2,6-hexanetriol; and $C_1$-$C_4$alkyl ethers of polyvalent alcohols, e.g. 2-methoxyethanol, 2-(2-methoxyethoxy)ethanol, 2-(2-ethoxyethoxy)ethanol, 2-[2-(2-methoxyethoxy)ethoxy]-ethanol or 2-[2-(2-ethoxyethoxy)ethoxy]ethanol; preferably N-methyl-2-pyrrolidone, diethylene glycol, glycerol or especially 1,2-propylene glycol, usually in an amount of from 2 to 30% by weight, especially from 5 to 30% by weight and preferably from 10 to 25% by weight, based on the total weight of the ink.

The inks may also comprise solubilisers, e.g. ε-caprolactam.

The printing inks may, inter alia for the purpose of adjusting the viscosity, comprise thickeners of natural or synthetic origin.

Furthermore, the pigment preparations according to the invention, especially when binder curing is to be effected by means of UV radiation, may comprise a photoinitiator which initiates the polymerisation.

Suitable photoinitiators for free radical photopolymerisations, that is to say the polymerisation of acrylates and, if desired, vinyl compounds, are e.g. benzophenone and benzophenone derivatives, such as 4-phenylbenzophenone and 4-chlorobenzophenone, acetophenone derivatives, such as 1-benzoylcyclohexan-1-ol, 2-hydroxy-2,2-dimethylacetophenone and 2,2-dimethoxy-2-phenylacetophenone, benzoin and benzoin ethers, such as methyl, ethyl and butyl benzoin ethers, benzil ketals, such as benzil dimethyl ketal, 2-methyl-1-[4-(methylthio)phenyl]-2-morpholinopropan-1-one, acylphosphine oxides, such as 2,4,6-trimethylbenzoyidiphenylphosphine oxide and bisacylphosphine oxides.

Suitable photoinitiators for cationic photopolymerisations, that is to say the polymerisation of vinyl compounds or epoxy-group-containing compounds, are, for example, aryldiazonium salts, such as 4-methoxybenzenediazonium hexafluorophosphate, benzenediazonium tetrafluoroborate and toluenediazonium tetrafluoroarsenate, aryliodonium salts, such as diphenyliodonium hexafluoroarsenate, arylsulfonium salts, such as triphenylsulfonium hexafluorophosphate, benzene- and toluene-sulfonium hexafluorophosphate and bis[4-diphenylsulfonio-phenyl]sulfide-bis-hexafluorophosphate, disulfones, such as diphenyl disulfone and phenyl-4-tolyl disulfone, diazodisulfones, imidotriflates, benzoin tosylates, isoquinolinium salts, such as N-ethoxyisoquinolinium hexafluorophosphate, phenyl-pyridinium salts, such as N-ethoxy-4-phenylpyridinium hexafluorophosphate, picolinium salts, such as N-ethoxy-2-picolinium hexafluorophosphate, ferrocenium salts, and titanocenes.

When a photoinitiator is present in the ink compositions according to the invention, which is generally necessary for binder curing by UV radiation, the content thereof is generally from 0.1 to 10% by weight, preferably from 0.1 to 8% by weight.

Examples of thickeners that may be mentioned include commercially available alginate thickeners, starch ethers or locust bean flour ethers, especially sodium alginate on its own or in admixture with modified cellulose, for example methyl-, ethyl-, carboxymethyl-, hydroxyethyl-, methylhydroxyethyl-, hydroxypropyl- or hydroxypropylmethyl-cellulose, especially having preferably from 20 to 25% by weight carboxymethylcellulose. Synthetic thickeners that may be mentioned are, for example, those based on poly(meth)acrylic acids or poly(meth)acrylamides.

The inks comprise such thickeners e.g. in an amount of from 0.01 to 2% by weight, especially from 0.01 to 1% by weight and preferably from 0.01 to 0.5% by weight, based on the total weight of the ink.

It is also possible for the inks to comprise buffer substances, for example borax, borate, phosphate, polyphosphate or citrate. Examples include borax, sodium borate, sodium tetraborate, sodium dihydrogen phosphate, disodium hydrogen phosphate, sodium tripolyphosphate, sodium pentapolyphosphate and sodium citrate. They are used especially in amounts of from 0.1 to 3% by weight, preferably from 0.1 to 1% by weight, based on the total weight of the ink, in order to establish a pH value of e.g. from 4 to 9, especially from 5 to 8.5.

As further additives, the inks may comprise surfactants or humectants.

As surfactants there come into consideration the commercially available anionic or non-ionic surfactants. Suitable humectants in the inks according to the invention include, for example, urea or a mixture of sodium lactate (advantageously in the form of a 50 to 60% aqueous solution) and glycerol and/or propylene glycol in amounts of preferably from 0.1 to 30% by weight, especially from 2 to 30% by weight.

Furthermore, the inks may also comprise customary additives, for example preservatives (such as glutaric dialdehyde and/or tetramethylolacetyleneurea), anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. Such agents are usually used in amounts of from 0.01 to 1% by weight, based on the total weight of the ink.

The inks can be prepared in customary manner by mixing together the individual constituents in the desired amount of water.

The inks according to the invention are especially suitable for use in recording systems of the kind in which an ink is expressed from a small opening in the form of droplets which are directed towards a substrate on which an image is formed. Suitable substrates are, for example, paper, textile fibre materials, metal foils or plastics foils. Suitable recording systems are e.g. commercially available ink-jet printers for use in paper or textile printing.

Depending upon the nature of the use, it may be necessary for e.g. the viscosity or other physical properties of the ink, especially those properties which influence the affinity of the ink for the substrate in question, to be adapted accordingly.

In ink-jet printing, individual droplets of ink are sprayed onto a substrate in a controlled manner from a nozzle. For this purpose, predominantly the continuous ink-jet method and the drop-on-demand method are used. In the continuous ink-jet method, the droplets are produced continuously and any droplets not required for the printing are conveyed to a collecting vessel and recycled. In the drop-on-demand method, however, droplets are produced and printed as required; that is to say droplets are produced only when required for the printing. The production of the droplets can be effected, for example, by means of a piezo-inkjet head or by means of thermal energy (bubble jet).

The subsequent curing of the binder, that is to say the fixing of the print, can be effected in customary manner with the aid of heat or high-energy radiation. For this purpose, the print is irradiated either with electrons under an inert gas atmosphere (e.g. nitrogen) (electron beam curing) or with high-energy electromagnetic radiation, preferably in a wavelength range of from 220 to 450 nm. In such a procedure, the chosen light intensities should be matched to the curing speed in order to avoid decomposition of the indicator.

When ink-jet printing is used, the procedure is advantageously as follows:

In Step a), a time-temperature indicator comprising at least one component of the above-described time temperature indicator being selected from the group consisting of the capped diazonium component, the coupling component and the photolatent acid is applied by means of ink-jet printing to the substrate, especially to the packaging of ageing- and temperature-sensitive products or to labels that are applied to the packaging.

In a preferred embodiment, in Step a) it is possible additionally to apply, by means of ink-jet printing, a reference scale which reproduces the change in the colour of the indicator as a function of time, and it is possible to apply, preferably in black ink, further text (or information), such as an expiry date, product identification, weight, contents etc.

Step a) is followed by Step b), activation, especially photo-induced acidification of the indicator to start the azo coupling reaction. The photo-induced curing of the binder advantageously includes the photo-induced initiation of the indicator.

Step c) is followed by the application of a protector, especially a color filter, which prevents renewed or ongoing photo-induced acidification of the indicator. In the case of the use of UV-sensitive photolatent acids, there come into consideration yellow filters which are permeable only to light having typical wavelengths of more than 430 nm. Advantageously the protective film, that is to say the color filter, can likewise be applied by means of ink-jet printing.

By means of the reference scale printed with the time-temperature indicator, absolute determination of quality grades is possible. The time-temperature indicator and the reference scale are advantageously arranged on a light-coloured substrate in order to facilitate reading.

Suitable substrate materials are both inorganic and organic materials, preferably those known from conventional layer and packaging techniques. There may be mentioned by way of example polymers, glass, metals, paper, cardboard etc.

The substrate can simultaneously form the packaging material for the perishable products or it can be applied to the packaging material, for example in the form of a label.

For example, in Step a) a printing ink, a printing ink concentrate and/or an ink-jet ink comprising a time-temperature indicator described above can be applied to the packaging of ageing- and temperature-sensitive products in the form of a barcode. The time- and/or temperature-induced coloration of the indicator is advantageously so adjusted that once the expiry date has been passed, the barcode can no longer be read by a scanner. Alternatively, the time- and/or temperature-dependent coloration of the indicator can also bring about a change in the barcode such that it can still be read, but, on being read, the information relating to the expiry date is given.

A prerequisite for the above-described time- and/or temperature-dependent visualisation of a barcode is, however, that the application of the indicator and its possible activation by irradiation are followed by the application of a protector, e.g. a colour filter, which prevents renewed or ongoing photo-induced acidification of the indicator.

In further applications, the method according to the invention allows counterfeit-proof marking of documents as originals in a variety of ways. For example, identification papers, passports, banknotes, cheques and share certificates can be marked as being originals. The method according to the invention can equally be used for creating counterfeit-proof product identification labels. The economic damage caused to the global economy by product piracy and counterfeit goods is immense. It is necessary particularly to prevent counterfeiting in the case of pharmaceutical products. The method according to the invention allows, for example, the counterfeit-proof marking of blister packs, so that it is possible to have a decisive effect in preventing inferior preparations being passed off as the original articles. There is extremely wide scope for use of the marking technology based on the method according to the invention. In addition to the labelling of branded products for mass consumption in order to ensure effective brand protection it is also possible for high-value goods that are at risk of counterfeiting, such as banknotes and chip cards, to be rendered counterfeit-proof in a simple and easily automated manner at relatively low cost. In the case of goods that are especially affected by product piracy, such as automotive spare parts, toys and CDs, it could be possible, in addition, to achieve copy protection that has been unachievable hitherto.

For example, a strip of an indicator that is not visible under normal circumstances could be applied to a suitable substrate of a product or document to be protected against counterfeiting. Checking the authenticity of the article could then be effected very simply by irradiation (e.g. with a lamp that emits light of a suitable wavelength), so that the indicator strip would be visible to an observer or, in the event of a counterfeit, not visible to the observer. The authenticity of branded products could also be checked in this way. It might be possible for the reproduction of a mark on packaging to be so changed under the action of light of a certain intensity and/or a certain wavelength spectrum that a consumer would be in no doubt as to the origin of the goods. Limits will thus be set on brand and/or product piracy.

The above-described principle of counterfeit protection by means of the method according to the invention can also be used for protection against pirate copies, where the original is duplicated by irradiation with light using a copier, scanner etc. For example, a banknote could be provided with an invisible indicator strip which would become visible under the action of light during the copying operation and thus would clearly identify a copy as such.

The invention accordingly relates also to a method for the counterfeit-proof labelling of products, which comprises the step of printing onto a product or onto the packaging of a product at least one time temperature indicator with chromic properties based on an azo coupling reaction between a capped diazonium component and a coupling component, wherein the product label is capable of being rendered visible by activation, especially by photo-induced acidification of the indicator.

EXAMPLES (1) Preparation of the Diazonium Salt 9.3 parts of weight of freshly destined compound 1 are emulsified in 84 parts of weight of water. The emulsion is cooled down to 0° C. under stirring und 8.5 parts of weight of $NaNO_2$ and 29 parts of weight of hydrochloric acid (w=0.32) are added. The mixture is stirred for another hour at 0° C.<T<5° C. Afterwards any excess of nitrite still present is destroyed following the addition of a small amount of sulfamide acid. An aqueous solution containing 14.1 parts of weight of phenyldiazoniumchloride is obtained.

Further diazonium salt solutions can be obtained in an analogous manner when reacting an amine compound according to Table 1:

TABLE 1

| # | Amine structure | Amine | parts of weight | Diazonium salt | parts of weight |
|---|---|---|---|---|---|
| 1 | (phenylamine structure) | Phenylamine (1)<br>MW = 93.13<br>MF = C₆H₇N | 9.3 | Phenyldiazoniumchloride | 14.1 |
| 2 | (4-nitroaniline structure) | 4-Nitro-phenylamine<br>MW = 138.13<br>MF = C₆H₆N₂O₂ | 13.8 | 4-Nitro-phenyldiazoniumchloride | 18.6 |
| 3 | (sulfanilic acid Na salt structure) | 4-Amino-benzenesulfonic acid, sodium salt<br>MW = 195.17<br>MF = C₆H₆NNaO₃S | 19.5 | 4-Sulfo-phenyldiazoniumchloride | 24.3 |
| 4 | (2-aminobenzenesulfonic acid Na salt structure) | 2-Amino-benzenesulfonic acid, sodium salt<br>MW = 195.17<br>MF = C₆H₆NNaO₃S | 19.5 | 2-Sulfo-phenyldiazoniumchloride | 24.3 |
| 5 | (4-amino-benzene-1,3-disulfonic acid disodium salt structure) | 4-Amino-benzene-1,3-disulfonic acid, disodium salt<br>MW = 297.22<br>MF = C6H5NNa2O6S2 | 29.7 | 2,4-Disulfo-phenyldiazoniumchlorid | 34.5 |
| 6 | (2-(3-amino-4-methoxy-benzenesulfonyl)-ethanol structure) | 2-(3-Amino-4-methoxy-benzenesulfonyl)-ethanol<br>MW = 231.27<br>MF = C₉H₁₃NO₄S | 23.1 | 5-[5-(2-Hydroxy-ethanesulfonyl)-2-methoxy-phenyldiazoniumchloride | 27.9 |
| 7 | (4-acetylamino-2-amino-benzenesulfonic acid Na salt structure) | 4-Acetylamino-2-amino-benzenesulfonic acid, sodium salt<br>MW = 252.23<br>MF = C₈H₉N₂NaO₄S | 25.2 | 5-Acetamido-2-sulfo-phenyldiazoniumchloride | 30.0 |
| 8 | (2-amino-5-methoxy-benzenesulfonic acid Na salt structure) | 2-Amino-5-methoxy-benzenesulfonic acid, sodium salt<br>MW = 225.20<br>MF = C₇H₈NNaO₄S | 22.5 | 4-Methoxy-2-sulfo-phenyldiazoniumchloride | 27.3 |
| 9 | (2-amino-naphthalene-1,5-disulfonic acid disodium salt structure) | 2-Amino-naphthalene-1,5-disulfonic acid, disodium salt<br>MW = 347.28<br>MF = C10H7NNa2O6S2 | 34.7 | 1,5-Disulfo-naphth-2-yl-diazoniumchloride | 39.5 |
| 10 | (5-amino-2,4-dimethyl-benzenesulfonic acid Na salt structure) | 5-Amino-2,4-dimethyl-benzene-sulfonic acid, sodium salt<br>MW = 223.23<br>MF = C₈H₁₀NNaO₃S | 20.1 | 1,3-Dimethyl-5-sulfo-phenyl-diazoniumchloride | 24.9 |

TABLE 1-continued

| | Amine | | parts of weight | Diazonium salt | parts of weight |
|---|---|---|---|---|---|
| 11 | [structure: NaO₃S-naphthalene-NH₂] | 4-Amino-naphthalene-1-sulfonic acid, sodium salt MW = 245.23 MF = $C_{10}H_8NNaO_3S$ | 24.5 | 4-Sulfo-naphth-1-yl-diazoniumchloride | 29.3 |

It will be understood that any other aromatic amine diazotizable with sodium nitrite can also be used.

(2) Preparation of the Triazine Intermediate 11.1 parts of weight of A are dissolved in 100 parts of weight of water at a pH between 9 and 11. The solution is cooled down to 0° C. under stirring. The diazonium salt solution prepared according to (1) is slowly added in a dropwise manner. The pH of the solution is maintained at 9<pH<11 by adding sodium hydroxide. The solution is stirred at 0° C.<T<5° C. for another hour and is then diluted with ice cold water up to a total volume of 215 ml. An aqueous solution containing 21.5 parts of weight of the sodium salt of 1-phenyl-3-(carboxymethane)-triazene is obtained.

Further triazene solutions can also be obtained in an analogous manner when reacting an amine compound according to Table 2:

TABLE 2

| | Amine | | Parts of weight | Triazene | | Example |
|---|---|---|---|---|---|---|
| A | [structure] | Methylamino-acetic acid, sodium salt (A) MW = 111.08 MF = $C_3H_6NNaO_2$ | 11.1 | [structure] | 3-(Carboxymethane)-1-Phenyl-triazene, sodium salt MW = 215.19 MF = $C_9H_{10}N_3NaO_2$ | 1A |
| B | [structure] | Methylamino-methanesulfonic acid, sodium salt MW = 147.13 MF = $C_2H_6NNaO_3S$ | 14.7 | [structure] | 1-Phenyl-3-(sulfomethane)-triazene, sodium salt MW = 237.21 MF = $C_7H_8N_3NaO_3S$ | 1B |
| C | [structure] | (Sulfomethyl-amino)-methane-sulfonic acid, disodiumsalt MW = 249.17 MF = $C_2H_5NNa_2O_6S_2$ | 24.9 | [structure] | 1-Phenyl-3,3-bis-(sulfomethane)-triazene, disodium salt MW = 353.29 MF = $C_8H_9N_3Na_2O_6S_2$ | 1C |
| D | [structure] | Methylamino-acetic acid, methyl ester MW = 103.12 MF = $C_4H_9NO_2$ | 10.3 | [structure] | 3-(Carboxymethyl-methane)-1-phenyl-triazene, sodium salt MW = 207.23 MF = $C_{10}H_{13}N_3O_2$ | 1D |
| E | [structure] | 2-Methylamino-ethanol MW = 75.11 MF = $C_3H_9NO$ | 7.5 | [structure] | 3-(2-Hydroxyethane)-1-phenyl-triazene MW = 179.22 MF = $C_9H_{13}N_3O$ | 1E |
| F | [structure] | Phenylamino-acetic acid, sodium salt MW = 173.15 MF = $C_8H_8NNaO_2$ | 17.3 | [structure] | 1,3-Diphenyl-3-(carboxymethane)-triazene, sodium salt MW = 277.26 MF = $C_{14}H_{12}N_3NaO_2$ | 1F |

Further triazene solutions NM (N=2-11 in Table 1, M=A-F in Table 2) are obtainable by reacting the diazonium salt solutions 2 to 9 with the amines A to F according to Table 3.

TABLE 3

| Amine | Amine | Triazene |
|---|---|---|
| 2 | A | 3-(Carboxymethane)-1-(4-nitro-phenyl)-triazene, sodium salt |
| 2 | B | 1-(4-Nitro-phenyl)-3-(sulfomethane)-triazene, sodium salt |
| 2 | C | 1-(4-Nitro-phenyl)-3,3-bis-(sulfomethane)-triazene, disodium salt |
| 2 | D | 3-(Carboxymethylmethane)-1-(4-nitrophenyl)-triazene, sodium salt |
| 2 | E | 3-(2-Hydroxyethane)-1-(4-nitrophenyl)-triazene |
| 2 | F | 3-(Carboxymethane)-1-(4-nitro-phenyl)-3-phenyl-triazene, sodium salt |
| 3 | A | 3-(Carboxymethane)-1-(4-sulfo-phenyl)-triazene, sodium salt |
| 3 | B | 1-(4-Sulfo-phenyl)-3-(sulfomethane)-triazene, sodium salt |
| 3 | C | 1-(4-Sulfo-phenyl)-3,3-bis-(sulfomethane)-triazene, disodium salt |
| 3 | D | 3-(Carboxymethylmethane)-1-(4-sulfophenyl)-triazene, sodium salt |
| 3 | E | 3-(2-Hydroxyethane)-1-(4-sulfophenyl)-triazene |
| 3 | F | 3-(Carboxymethane)-1-(4-sulfo-phenyl)-3-phenyl-triazene, sodium salt |
| 4 | A | 3-(Carboxymethane)-1-(2-sulfo-phenyl)-triazene, sodium salt |
| 4 | B | 1-(2-Sulfo-phenyl)-3-(sulfomethane)-triazene, sodium salt |
| 4 | C | 1-(2-Sulfo-phenyl)-3,3-bis-(sulfomethane)-triazene, disodium salt |
| 4 | D | 3-(Carboxymethylmethane)-1-(2-sulfophenyl)-triazene,sodium salt |
| 4 | E | 3-(2-Hydroxyethane)-1-(2-sulfophenyl)-triazene |
| 4 | F | 3-(Carboxymethane)-1-(2-sulfo-phenyl)-3-phenyl-triazene, sodium salt |
| 5 | A | 3-(Carboxymethane)-1-(2,4-disulfo-phenyl)-triazene, sodium salt |
| 5 | B | 1-(2,4-Disulfo-phenyl)-3-(sulfomethane)-triazene, sodium salt |
| 5 | C | 1-(2,4-Disulfo-phenyl)-3,3-bis-(sulfomethane)-triazene, disodium salt |
| 5 | D | 3-(Carboxymethylmethane)-1-(2,4-disulfophenyl)-triazene, sodium salt |
| 5 | E | 3-(2-Hydroxyethane)-1-(2,4-disulfophenyl)-triazene |
| 5 | F | 3-(Carboxymethane)-1-(2,4-disulfo-phenyl)-3-phenyl-triazene, sodium salt |
| 6 | A | 3-(Carboxymethane)-1-(5-[5-(2-Hydroxy-ethanesulfonyl)-2-methoxy-phenyl)-triazene, sodium salt |
| 6 | B | 1-(5-[5-(2-Hydroxy-ethanesulfonyl)-2-methoxy-phenyl)-3-(sulfomethane)-triazene, sodium salt |
| 6 | C | 1-(5-[5-(2-Hydroxy-ethanesulfonyl)-2-methoxy-phenyl)-3,3-bis-(sulfomethane)-triazene, disodium salt |
| 6 | D | 3-(Carboxymethylmethane)-1-(5-[5-(2-Hydroxy-ethanesulfonyl)-2-methoxy-phenyl)-triazene, sodium salt |
| 6 | E | 3-(2-Hydroxyethane)-1-(5-[5-(2-Hydroxy-ethanesulfonyl)-2-methoxy-phenyl)-triazene |
| 6 | F | 3-(Carboxymethane)-1-(5-[5-(2-Hydroxy-ethanesulfonyl)-2-methoxy-phenyl)-3-phenyl-triazene, sodium salt |
| 7 | A | 3-(Carboxymethane)-1-(5-acetamido-2-sulfo-phenyl)-triazene, sodium salt |
| 7 | B | 1-(5-Acetamido-2-sulfo-phenyl)-3-(sulfomethane)-triazene, sodium salt |
| 7 | C | 1-(5-Acetamido-2-sulfo-phenyl)-3,3-bis-(sulfomethane)-triazene, disodium salt |
| 7 | D | 3-(Carboxymethylmethane)-1-(5-acetamido-2-sulfo-phenyl)-triazene, sodium salt |
| 7 | E | 3-(2-Hydroxyethane)-1-(5-acetamido-2-sulfo-phenyl)-triazene |
| 7 | F | 3-(Carboxymethane)-1-(5-acetamido-2-sulfo-phenyl)-3-phenyl-triazene, sodium salt |
| 8 | A | 3-(Carboxymethane)-1-(4-methoxy-2-sulfo-phenyl)-triazene, sodium salt |
| 8 | B | 1-(4-Methoxy-2-sulfo-phenyl)-3-(sulfomethane)-triazene, sodium salt |
| 8 | C | 1-(4-Methoxy-2-sulfo-phenyl)-3,3-bis-(sulfomethane)-triazene, disodium salt |
| 8 | D | 3-(Carboxymethylmethane)-1-(4-methoxy-2-sulfo-phenyl)-triazene, sodium salt |
| 8 | E | 3-(2-Hydroxyethane)-1-(4-methoxy-2-sulfo-phenyl)-triazene |
| 8 | F | 3-(Carboxymethane)-1-(4-methoxy-2-sulfo-phenyl)-3-phenyl-triazene, sodium salt |
| 9 | A | 3-(Carboxymethane)-1-(1,5-disulfo-naphth-2-yl-)-triazene, sodium salt |
| 9 | B | 1-(1,5-disulfo-naphth-2-yl-)-3-(sulfomethane)-triazene, sodium salt |
| 9 | C | 1-(1,5-disulfo-naphth-2-yl-)-3,3-bis-(sulfomethane)-triazene, disodium salt |
| 9 | D | 3-(Carboxymethyl methane)-1-(1,5-disulfo-naphth-2-yl-)-triazene, sodium salt |
| 9 | E | 3-(2-Hydroxyethane)-1-(1,5-disulfo-naphth-2-yl-)-triazene |
| 9 | F | 3-(Carboxymethane)-1-(1,5-disulfo-naphth-2-yl-)-3-phenyl-triazene, sodium salt |
| 10 | A | 3-(Carboxymethane)-1-(1,3-dimethyl-5-sulfo-phenyl-)-triazene, sodium salt |

TABLE 3-continued

| Amine | Amine | Triazene |
|---|---|---|
| 10 | B | 1-(1,3-dimethyl-5-sulfo-phenyl-)-3-(sulfomethane)-triazene, sodium salt |
| 10 | C | 1-(1,3-dimethyl-5-sulfo-phenyl-)-3,3-bis-(sulfomethane)-triazene, disodium salt |
| 10 | D | 3-(Carboxymethylmethane)-1-(1,3-dimethyl-5-sulfo-phenyl-)-triazene, sodium salt |
| 10 | E | 3-(2-Hydroxyethane)-1-(1,3-dimethyl-5-sulfo-phenyl-)-triazene |
| 10 | F | 3-(Carboxymethane)-1-(1,3-dimethyl-5-sulfo-phenyl-)-3-phenyl-triazene, sodium salt |
| 11 | A | 3-(Carboxymethane)-1-(4-sulfo-naphth-1-yl-)-triazene, sodium salt |
| 11 | B | 1-(4-sulfo-naphth-1-yl-)-3-(sulfomethane)-triazene, sodium salt |
| 11 | C | 1-(4-sulfo-naphth-1-yl-)-3,3-bis-(sulfomethane)-triazene, disodium salt |
| 11 | D | 3-(Carboxymethylmethane)-1-(4-sulfo-naphth-1-yl-)-triazene, sodium salt |
| 11 | E | 3-(2-Hydroxyethane)-1-(4-sulfo-naphth-1-yl-)-triazene |
| 11 | F | 3-(Carboxymethane)-1-(4-sulfo-naphth-1-yl-)-3-phenyl-triazene, sodium salt |

It will be understood that any other secondary amine capable to react with a diazonium salt solution under formation of a triazene can also be used.

(3) Preparation of the Time Temperature Indicator 5 g sodium tripolyphosphate and 1 g ethylenediamine tetraacetic acid (EDTA) are dissolved in 1.2 l of hot water, cooled down to room temperature, splitted into portions of 10 ml and adjusted to a pH of a desired value of 4<pH<10 with hydrochloric acid and/or sodium hydroxide. Optionally another buffer system capable to maintain a sufficient stable pH as desired may be employed.

10 ml of a buffer solution having a pH of 4<pH<10 are added to 1 ml of a solution containing 21.5 parts of weight of the sodium salt of 1-phenyl-3-(2-carboxymethane)-triazene prepared according to (2). 0.11 parts of weight of the sodium salt of 6-hydroxy-naphthalene-2-sulfonic acid (I) are added to the resulting solution and the solution is then printed on a suitable carrier.

Depending on the chosen pH value, the time and the surrounding temperature the carrier adopts a shiny orange color due to the formation of the sodium salt of 6-hydroxy-5-phenylazo-naphthalene-2-sulfonic acid (=Food Orange 1; C.I. F OR 001):

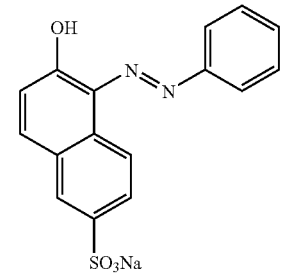

6-Hydroxy-5-phenylazo-naphthalene-2-sulfonic acid, sodium salt=C.I. F OR 001

MW=350.33

MF=$C_{16}H_{11}N_2NaO_4S$

Further time-temperature indicators NMI (N=1-11 in Table 1, M=A-F in Table 2, I=I-V in Table 4) are obtainable by reacting the triazene solutions described in Tables 2 and 3 with the coupling components according to Table 4.

TABLE 4

| I | | 6-Hydroxy-naphthalene-2-sulfonic acid, sodium salt<br>MW = 246.22<br>MF = $C_{10}H_7NaO_4S$ |
|---|---|---|
| II | | Benzene-1,3-diol<br>MW = 110.11<br>MF = $C_6H_6O_2$ |
| III | | 4-Hydroxy-naphthalene-1-sulfonic acid sodium salt<br>MW = 246.22<br>MF = $C_{10}H_7NaO_4S$ |

TABLE 4-continued

| | | |
|---|---|---|
| IV | 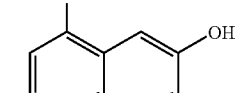 | 7-Hydroxy-naphthalene-1,3,6-trisulfonic acid, trisodium salt<br>MW = 450.31<br>MF = $C_{10}H_5Na_3O_{10}S_3$ |
| V | 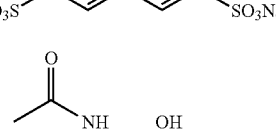 | 4-Acetylamino-5-hydroxy-naphthalene-2,7-disulfonic acid, disodium salt<br>MW = 405.32<br>MF = $C_{12}H_9NNa_2O_8S_2$ |

It will be understood that any other organic coupling component capable to undergo an electrophilic reaction with a diazonium cation under the formation of an azo group can also be used.

It will further be understood that instead of the sodium salts described above, any other cation salt may also be employed.

The invention claimed is:

1. A method of printing a substrate, comprising
(a) printing onto the substrate at least one time temperature indicator with chromic properties based on an azo coupling reaction between a capped diazonium component and a coupling component, and after step (a),
(b) activating the time temperature indicator by lowering the pH to a value of from 6.5 to 1.5 by conversion of a photolatent acid into an active acid catalyst by irradiation with short-wave light of wavelengths between 150 nm and 1500 nm.

2. The method according to claim 1, wherein the capped diazonium component is a compound of formula (1), (2), (3), (4) or (5)

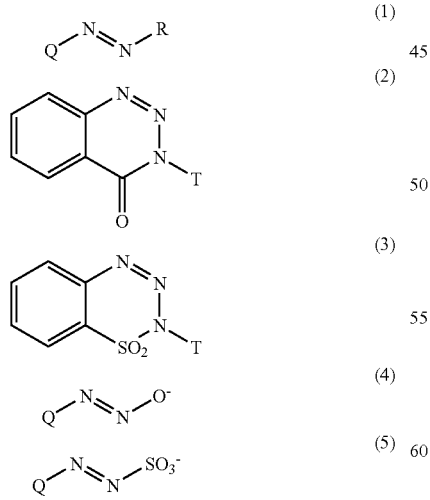

wherein
Q is a radical of an organic compound,
R is the radical of an unsubstituted or substituted aliphatic or aromatic amine, and T is an unsubstituted or substituted, aliphatic or aromatic residue.

3. The method according to claim 1, wherein the capped diazonium component is a compound of general formula:

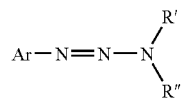

wherein Ar stands for an optionally substituted aryl or heteroaryl residue; and
wherein R' and R" stand independently from each other for a linear or branched $C_1$-$C_6$alkyl, which is optionally substituted by one or two identical or different substituents selected from the group consisting of COOH, OH, halogen, $SO_3H$, $NH_2$, $NH(C_1$-$C_2$alkyl) and $N(C_1$-$C_2$alkyl)$_2$.

4. The method according to claim 1, wherein the coupling component is an unsubstituted or substituted benzene or naphthalene, an open-chain methylene-active compound, or an unsubstituted or substituted heterocyclic compound.

5. The method according to claim 1, wherein the capped diazonium component and the coupling component are moieties of a single compound.

6. The method according to claim 5, wherein the single compound is a compound of formula (6)

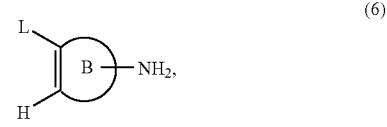

wherein
L is hydroxy or $NHL_1$, $L_1$ being hydrogen or $C_1$-$C_4$alkyl, and B is an aromatic or heterocyclic ring.

7. The method according to claim 6, wherein the single compound is selected from the group consisting of

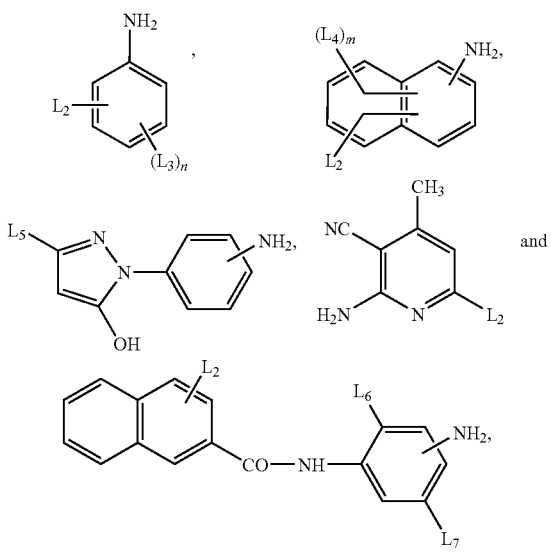

wherein
L$_2$ is hydroxy or NHL$_1$, L$_1$ being hydrogen or C$_1$-C$_4$alkyl, L$_3$ is C$_1$-C$_4$alkyl or sulfo, L$_4$ is hydroxy or sulfo, L$_5$ is hydrogen, C$_1$-C$_4$alkyl, —COOH or COOC$_1$-C$_4$alkyl, L$_6$ and L$_7$ are, each independently of the other, hydrogen or C$_1$-C$_4$alkoxy, n is a number 0, 1 or 2, and m is a number 0, 1 or 2.

8. The method according to claim 1, wherein the capped diazonium component and the coupling component are capable of performing multiple azo coupling reactions leading to azo dyes containing more than one azo moiety.

9. The method according to claim 1, wherein step (b) comprises printing onto the substrate a photolatent acid solution.

10. The method according to claim 9, wherein the photolatent acid is selected from the group consisting of oxime sulfonate compounds, alpha-sulfonyloxy carbonyl compounds, N-sulfonyloxyimide compounds, o-nitrobenzylsulfonate compounds and pyrogallol sulfonate compounds.

11. A printing ink or printing ink concentrate, comprising as components of a time temperature indicator with chromic properties based on an azo coupling reaction, a capped diazonium component, a coupling component and a photolatent acid.

12. A method of determining the quality of an ageing- and temperature-sensitive product, which comprises the following steps:
a) printing onto a substrate at least one time temperature indicator with chromic properties based on an azo coupling reaction between a capped diazonium component and a coupling component,
b) activating the indicator by photo-induced acidification of the indicator,
c) optionally applying of a protector which prevents continued photo-induced acidification of the indicator, and
d) determining the degree of time- or temperature-induced coloration and deducing the quality of the product from the degree of coloration.

13. A method for the counterfeit-proof labelling of products, comprising printing onto a product or onto the packaging of a product at least one time temperature indicator with chromic properties based on an azo coupling reaction between a capped diazonium component and a coupling component, wherein the product label is capable of being rendered visible by activation by photo-induced acidification of the indicator.

14. The method according to claim 3, wherein Ar stands for an optionally substituted phenyl, naphthyl, pyrrolyl, furyl, thiophenyl, oxazolyl, isoxazolyl, thiazolyl, pyrazolyl and pyridinyl; and
wherein R' and R" stand independently from each other for a group selected from methyl,

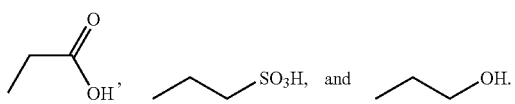

15. The method according to claim 1, wherein in step (b) the time temperature indicator is activated by lowering the pH to a value of from 4 to 3.

16. The method according claim 1, wherein step (b) comprises the conversion of the photolatent acid into an active acid catalyst by irradiation with short-wave light of wavelengths between 250 nm and 450 nm.

17. A printing ink or printing ink concentrate according to claim 11, wherein the capped diazonium component is a compound of general formula:

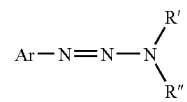

wherein Ar stands for an optionally substituted aryl or heteroaryl residue; and
R' and R" stand independently from each other for a linear or branched C$_1$-C$_6$alkyl, which is optionally substituted by one or two identical or different substituents selected from the group consisting of COOH, OH, halogen, SO$_3$H, NH$_2$, NH(C$_1$-C$_2$alkyl) and N(C$_1$-C$_2$alkyl)$_2$.

18. A printing ink or printing ink concentrate according to claim 17, wherein the capped diazonium component is a compound of general formula:

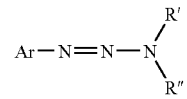

wherein Ar stands for an optionally substituted phenyl, naphthyl, pyrrolyl, furyl, thiophenyl, oxazolyl, isoxazolyl, thiazolyl, pyrazolyl and pyridinyl;
and/or wherein R' and R" stand independently from each other for methyl,

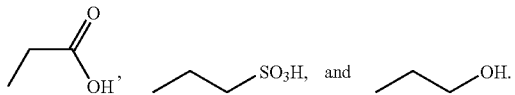

19. The method according to claim 1, wherein the coupling compound is selected from the group consisting of acylacetarylamides, phenols, naphthols, pyridones, quinolones, pyrazoles, indoles, diphenylamines, anilines, aminopyridines, pyrimidones, naphthylamines, aminothiazoles, thiophenes and hydroxypyridines.

* * * * *